ated under 35

United States Patent
Moshe

(10) Patent No.: US 7,378,855 B2
(45) Date of Patent: May 27, 2008

(54) BI-DIRECTIONAL THREE-DIMENSIONAL MICROWAVE SCANNING AND VOLUMETRIC MAPPING OF A WHOLE ROLL OR PALLET OF PAPER

(75) Inventor: Danny S. Moshe, Kiryat Ono (IL)

(73) Assignees: Malcam Ltd., Tel-Aviv (IL); Green Vision Systems Ltd., Tel-Aviv (IL)

( * ) Notice: Subject to any disclaimer, the term of this patent is extended or adjusted under 35 U.S.C. 154(b) by 27 days.

(21) Appl. No.: 11/587,624

(22) PCT Filed: May 1, 2005

(86) PCT No.: PCT/IL2005/000459

§ 371 (c)(1),
(2), (4) Date: Oct. 26, 2006

(87) PCT Pub. No.: WO2005/103738

PCT Pub. Date: Nov. 3, 2005

(65) Prior Publication Data

US 2007/0229093 A1 Oct. 4, 2007

Related U.S. Application Data

(60) Provisional application No. 60/564,943, filed on Apr. 26, 2004.

(51) Int. Cl.
*G01R 31/02* (2006.01)
*G01S 13/00* (2006.01)

(52) U.S. Cl. ............... 324/640; 324/639; 324/637; 342/22

(58) Field of Classification Search ............ 324/640, 324/639, 637, 629, 600, 634, 643, 664, 689, 324/694, 22
See application file for complete search history.

(56) References Cited

U.S. PATENT DOCUMENTS

| | | | |
|---|---|---|---|
| 5,621,330 A | 4/1997 | Greenwald et al. | |
| 5,933,014 A * | 8/1999 | Hartrumpf et al. | 324/642 |
| 6,107,809 A | 8/2000 | Moshe et al. | |
| 6,111,415 A | 8/2000 | Moshe | |
| 6,292,578 B1 | 9/2001 | Kalvin | |
| 6,411,106 B1 * | 6/2002 | Holmes et al. | 324/643 |
| 6,480,141 B1 | 11/2002 | Toth et al. | |
| 6,930,492 B2 * | 8/2005 | Moshe et al. | 324/637 |

* cited by examiner

*Primary Examiner*—Andrew H. Hirshfeld
*Assistant Examiner*—Hoai-An D. Nguyen

(57) ABSTRACT

Bi-directional (longitudinal and angular) three-dimensional volumetric microwave scanning of a whole roll or pallet of paper (FIGS. 3, 4), including three-dimensional volumetric mapping of internal properties and characteristics (moisture content, density, material uniformity, defects and types thereof, and variabilities thereof) of the roll or pallet of paper. Transmitted microwaves propagate through longitudinally and angularly defined portions of individual cross-sectional volumetric segments of the roll or pallet of paper. Microwave parameters (amplitude, phase) are perturbed by, and are a function of the internal properties and characteristics of, the contents of volumetric segment portions of the roll or pallet of paper. Microwave differential parameters (amplitude attenuation, phase shift) are calculated and used for calculating and determining values, relationships, two-dimensional graphs and maps, and, three-dimensional volumetric graphs and maps (FIGS. 5, 6), of the internal properties and characteristics of at least part of the roll or pallet of paper.

28 Claims, 5 Drawing Sheets

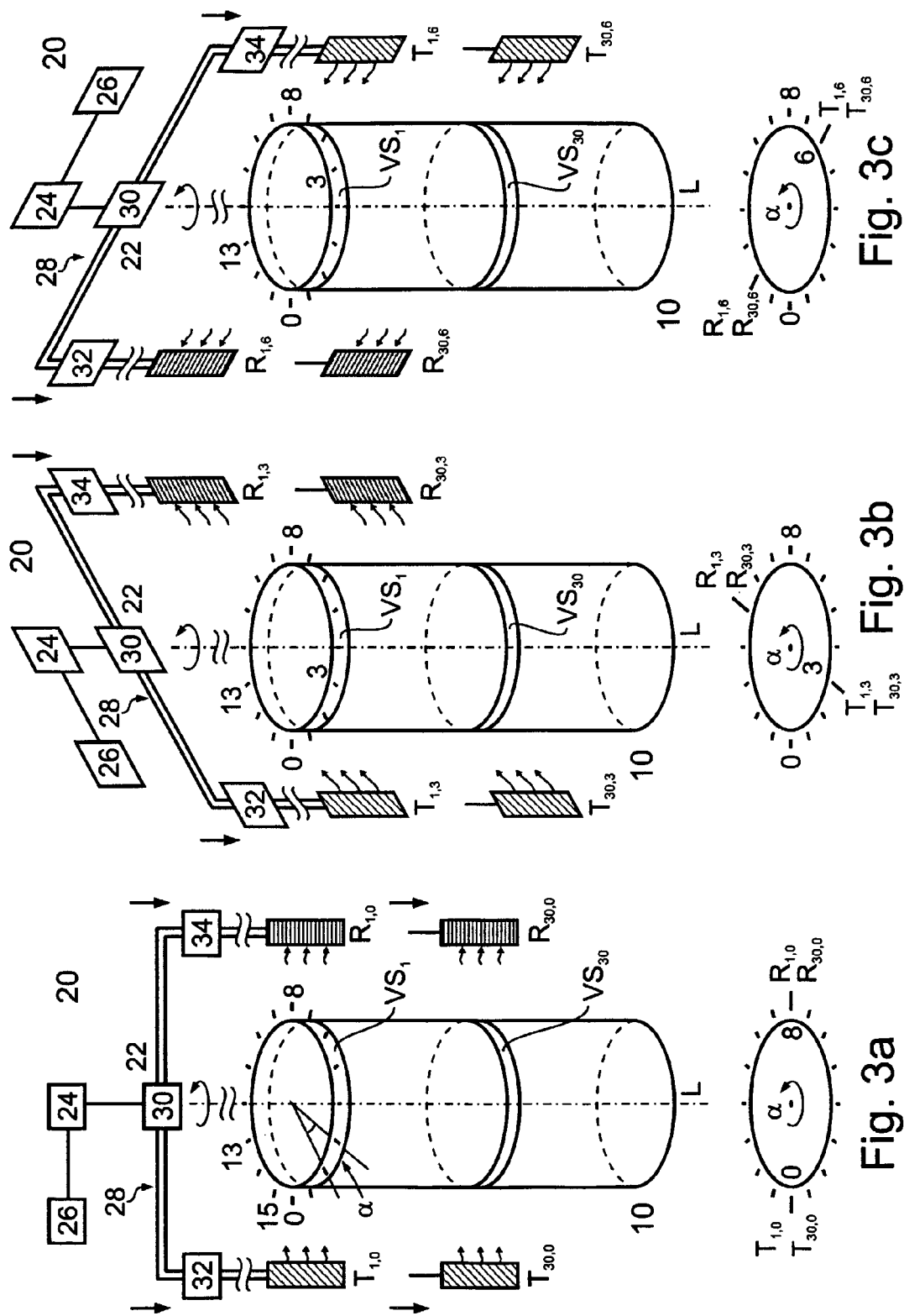

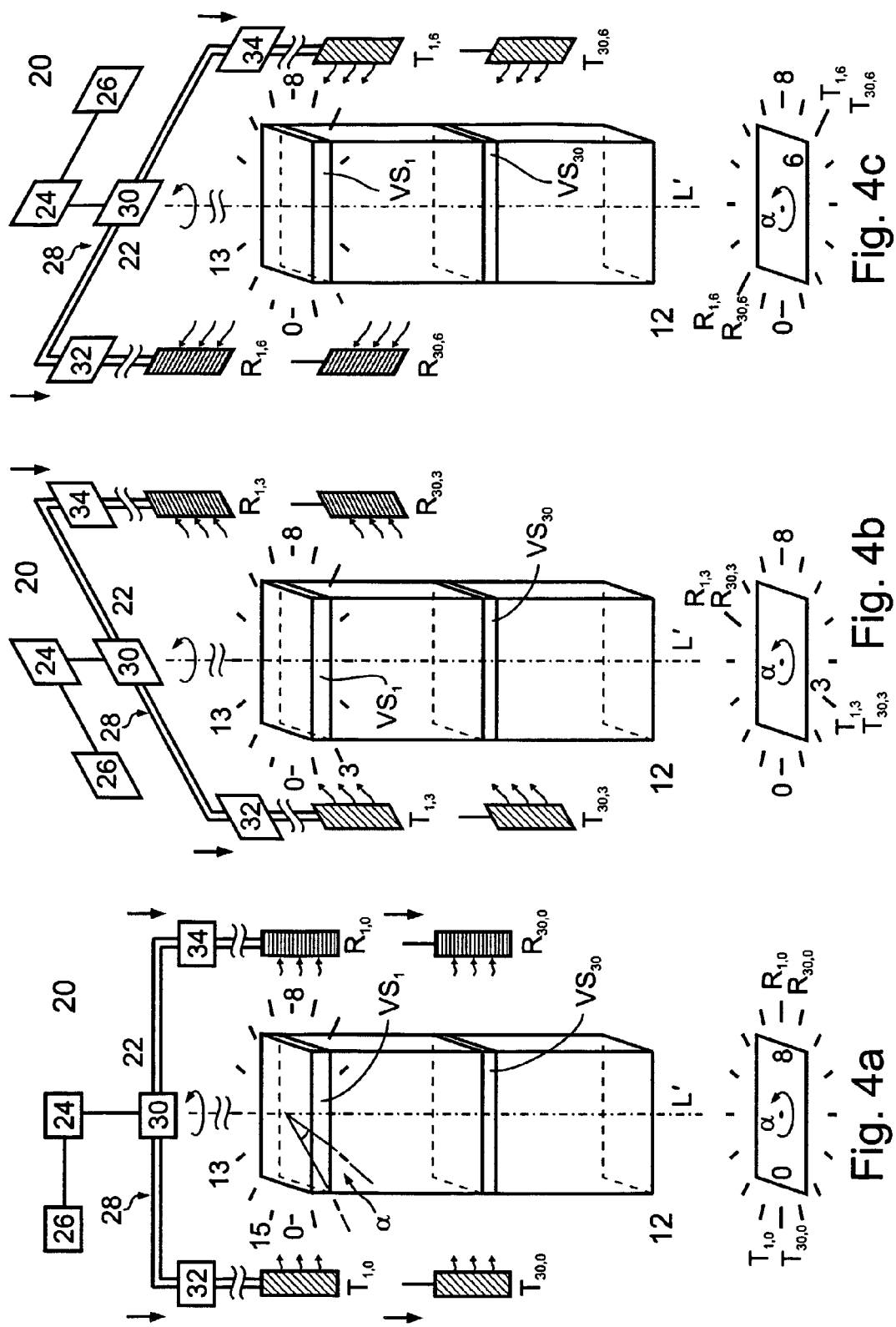

BI-DIRECTIONAL THREE-DIMENSIONAL MICROWAVE SCANNING AND VOLUMETRIC MAPPING OF A WHOLE ROLL OR PALLET OF PAPER

RELATED APPLICATIONS

This Application is a National Phase of PCT Patent Application No. PCT/IL2005/000459 having International Filing Date of May 1, 2005, which claims the benefit of U.S. Provisional Patent Application No. 60/564,943 filed on Apr. 26, 2004. The contents of the above Applications are all incorporated herein by reference.

FIELD AND BACKGROUND OF THE INVENTION

The present invention relates to microwave methods of measuring and analyzing internal properties and characteristics, such as moisture content, density, material uniformity, and, defects and types thereof, and variabilities thereof, of commercial sized whole rolls or pallets of paper, and more particularly, to a method of bi-directional (longitudinal and angular) three-dimensional microwave scanning of a whole roll or pallet of paper. The method of the present invention enables, and further includes, three-dimensional volumetric mapping of internal properties and characteristics of the whole roll or pallet of paper.

The present invention is particularly relevant and applicable to manufacturers, users, or/and further processors, of commercial sized 'whole' rolls or pallets of paper. Herein, a 'whole' roll or pallet of paper refers to a roll or pallet of paper as manufactured in its whole or entire final form, for example, having relatively bulky geometrical dimensions (diameter, height, length, width) on the order of about 1 meter. This is in contrast to a single portion or section of paper cut from a partly unrolled whole roll of paper, or, a single square or rectangular sheet or piece of paper separately taken from a whole pallet of stacked paper. Depending upon the thickness of the paper, a whole roll of paper having such geometrical dimensions can be unrolled to a total length of on the order of tens, or even hundreds, of meters. Similarly, a whole pallet of stacked paper having such geometrical dimensions can be unstacked to a total length of on the order of tens, or even hundreds, of meters.

Such relatively large sized whole rolls and pallets of paper are ordinarily manufactured in paper mills from bulk quantities of wood pulp or/and wood chips formed from cut lumber obtained from harvested and processed trees. Commercial sized whole rolls and pallets of paper serve as raw material for manufacturing paper and paper products, which involve subjecting the whole rolls or pallets of paper to a variety of different processes. Such processes typically involve cutting various lengths of unrolled paper from a whole roll of paper, or unstacking separate sheets or pieces of paper taken from a whole pallet of paper, pressing, additional cutting, printing, and packaging, and any number of other processes associated with manufacturing paper and paper products.

Herein, internal properties and characteristics, such as moisture content, density, material uniformity, and, defects and types thereof, and variabilities thereof, of a whole roll or pallet of paper refer to the global, bulk, or macroscopic, internal properties and characteristics, such as moisture content, density, material uniformity, and, defects and types thereof, and variabilities thereof, of a specified volumetric segment or number of volumetric segments of the whole roll or pallet of paper, including bulk or macroscopic volume occupied by air and moisture throughout the whole roll or pallet of paper, making up or forming the whole roll or pallet of paper. These internal properties and characteristics of the whole roll or pallet of paper are to be clearly distinguished from the local, molecular, or microscopic, properties and characteristics, such as molecular density, molecular structure, microscopic defects, and microscopic impurities, and variabilities thereof, of only the paper, excluding bulk or macroscopic volume occupied by air and moisture, making up or forming the whole roll or pallet of paper.

Once manufactured, each whole roll or pallet of paper has internal properties and characteristics, such as moisture content, density, material uniformity, and, defects and types thereof, and variabilities thereof, whose values may be outside of acceptable ranges or/and may undesirably change prior to the whole roll or pallet of paper being sent to, or used in, the next manufacturing process. During or/and following such a manufacturing sequence, it is critically important that these internal properties and characteristics of the whole roll or pallet of paper be determined and monitored, such as by employing quality control and quality assurance procedures. Data and information obtained from the quality control and quality assurance procedures are used for controlling or/and adjusting the internal properties and characteristics of the whole roll or pallet of paper, such as by employing process control and process feedback procedures, prior to the whole roll or pallet of paper being sent to, or used in, the next manufacturing process or storage, in order to assure proper characteristics and performance of the finished paper or finished paper products.

In particular, if one or more of the above indicated internal properties and characteristics of a given portion or section of the whole roll or pallet of paper is outside of established quality control or quality assurance values, use of such a portion or section of the whole roll or pallet of paper is expected to lead to downstream intermediate products, or stored roll or pallet of paper, similarly failing their established quality control values, potentially causing undesirable rejection of material, manufacturing down time, and added cost to an overall sequence of manufacturing paper or paper products. For example, in the case of manufacturing paper or paper products, if one or more of the above indicated internal properties and characteristics of a given portion or section of the whole roll or pallet of paper is outside of established quality control values, at least that portion or section of the whole roll or pallet of paper needs to be made note of for non-use or/and removal prior to the whole roll or pallet of paper continuing into further downstream processing or storage, otherwise, there will either be down time due to one or more paper press breaks, or 'below quality' paper or paper products ending up in the consumer marketplace, clearly undesirable to a manufacturer of paper or paper products, as well as undesirable to consumers of the paper or paper products.

Currently, manufacturers, users, or/and further processors, of commercial sized whole rolls and pallets of paper, employ point or localized types of non-invasive measurement and analysis methods, based on measuring and analyzing individual test points located on the external surface of a whole roll or pallet of paper, or located on a single portion or section of paper cut from an unrolled whole roll of paper, or located on a single square or rectangular piece of paper separately taken from a whole pallet of stacked paper. These non-invasive types of methods are capable of only roughly estimating internal properties and characteristics of a whole roll or pallet of paper. Such measurement and analysis methods are incapable or/and inapplicable for determining or generating three-dimensional volumetric maps of internal properties and characteristics, such as moisture content, density, material uniformity, and, defects and types thereof, and variabilities thereof, of a 'whole' roll or pallet of paper.

There is thus a need for, and it would be highly advantageous to have a method of bi-directional (longitudinal and angular) three-dimensional microwave scanning of a whole roll or pallet of paper. Additionally, there is need for such an invention which also enables, and further includes, three-dimensional volumetric mapping of internal properties and characteristics of the whole roll or pallet of paper.

SUMMARY OF THE INVENTION

The present invention relates to a method of bi-directional (longitudinal and angular) three-dimensional microwave scanning of a whole roll or pallet of paper. The method of the present also enables, and further includes, three-dimensional volumetric mapping of internal properties and characteristics, such as moisture content, density, material uniformity, and, defects and types thereof, and variabilities thereof, of the whole roll or pallet of paper.

Microwaves, having one or more constant or/and variable amplitudes or/and frequencies, are transmitted into, and propagate through, longitudinally and angularly defined portions of individual cross-sectional volumetric (three-dimensional) segments of a whole roll or pallet of paper, such that the parameters (amplitude, phase) of the propagating microwaves are perturbed by, and are a function of the internal properties and characteristics of, the contents of the volumetric segment portions of the whole roll or pallet of paper. At least a portion of the propagating microwaves exiting the opposite side of each cross-sectional volumetric segment is received. The parameters (amplitude, phase) of both the transmitted microwaves and the received microwaves are used for calculating the microwave differential parameters of amplitude attenuation and phase shift, which in turn, are used for calculating and determining values, relationships, two-dimensional graphs and maps, and, three-dimensional volumetric graphs and maps, of the internal properties and characteristics, such as moisture content, density, material uniformity, and, defects and types thereof, and variabilities thereof, of at least part of the whole roll or pallet of paper.

'Test' values of the microwave differential parameters, amplitude attenuation and phase shift, are calculated by analyzing the transmitted and received microwaves. This data is compared to 'calibration' values of corresponding microwave differential parameters obtained from a similarly analyzed reference roll or pallet of paper having known internal properties and characteristics. The sets of test and calibration microwave differential parameter data, along with sophisticated software based automatic pattern recognition (APR) and classification data analysis techniques, are used for generating meaningful data and information, in particular, values, relationships, two-dimensional graphs and maps, and, three-dimensional volumetric graphs and maps, of the internal properties and characteristics, such as moisture content, density, material uniformity, and, defects and types thereof, and variabilities thereof, of at least part of the whole roll or pallet of paper.

The generated data and information characterizing the whole roll or pallet of paper are directly applicable for optimally designing, performing, validating, analyzing, monitoring, QC/QA testing, controlling, and troubleshooting, of an overall paper or paper product manufacturing process, in a 'smart' (accurate, precise, and cost effective) manner.

For implementing each main aspect of the present invention, an exemplary microwave generating/transmitting/receiving/analyzing system, which includes a single robotic arms microwave generating/transmitting/receiving unit for holding, maneuvering, and (longitudinally and angularly) positioning, a single paired microwave transmitter and microwave receiver, is used as part of the automatic bi-directional (longitudinal and angular) three-dimensional microwave 'step-wise' scanning of cross-sectional volumetric segments of the whole roll or pallet of paper.

Thus, according to the present invention, there is provided a method of bi-directional (longitudinal and angular) three-dimensional microwave scanning of a whole roll or pallet of paper, comprising the steps of: (a) transmitting microwaves into a portion of a cross-sectional volumetric segment of the whole roll or pallet of paper, wherein the cross-sectional volumetric segment lies in a plane perpendicular to, and is centered around a longitudinal position located along, longitudinal axis of the roll or pallet of paper, such that the transmitted microwaves propagate within and through the portion, for forming transmitted microwaves associated with the portion of the volumetric segment; (b) receiving at least a portion of the propagating microwaves exiting opposite side of the volumetric segment, for forming received microwaves associated with the portion of the volumetric segment; (c) repeating steps (a) and (b), at end of each of a plurality of angular step sizes circumscribing around the volumetric segment, for forming a plurality of paired transmitted and received microwaves associated with a respective plurality of new portions of the volumetric segment, such that the portion and the new portions of the volumetric segment are each associated with a different angular position circumscribing around the same volumetric segment; and (d) repeating steps (a) through (c), for a plurality of longitudinal step sizes longitudinally extending along the longitudinal axis of the roll or pallet of paper, wherein each step size is associated with a respective new cross-sectional volumetric segment lying in a plane perpendicular to, and centered around a new longitudinal position located along, the longitudinal axis of the roll or pallet of paper, for forming a new plurality of the paired transmitted and received microwaves associated with the different angular positions circumscribing around each same new volumetric segment, for each of a plurality of the new volumetric segments, thereby completing a three-dimensional microwave scan of at least a part of the whole roll or pallet of paper.

According to further characteristics in preferred embodiments of the invention described below, a set of the pluralities of the paired transmitted and received microwaves associated with the different angular positions circumscribing around each of the volumetric segments of the roll or pallet of paper is used for three-dimensional volumetric mapping of internal properties and characteristics of the at least part of the whole roll or pallet of paper.

According to another aspect of the present invention, there is provided a method of three-dimensional volumetric mapping of internal properties and characteristics of a whole roll or pallet of paper, comprising the steps of: (a) transmitting microwaves into a portion of a cross-sectional volumetric segment of the whole roll or pallet of paper, wherein the cross-sectional volumetric segment lies in a plane perpendicular to, and is centered around a longitudinal position located along, longitudinal axis of the roll or pallet of paper, such that the transmitted microwaves propagate within and through the portion, for forming transmitted microwaves associated with the portion of the volumetric segment; (b) receiving at least a portion of the propagating microwaves exiting opposite side of the volumetric segment, for forming received microwaves associated with the portion of the volumetric segment; (c) repeating steps (a) and (b), at end of each of a plurality of angular step sizes circumscribing around the volumetric segment, for forming a plurality of paired transmitted and received microwaves associated with a respective plurality of new portions of the volumetric segment, such that the portion and the new portions of the volumetric segment are each associated with a different angular position circumscribing around the same volumetric segment; (d) repeating steps (a) through (c), for a plurality of longitudinal step sizes longitudinally extending along the longitudinal axis of the roll or pallet of paper, wherein each step size is associated with a respective new cross-sectional volumetric segment lying in a plane perpendicular to, and centered around a new longitudinal position located along, the longitudinal axis of the roll or pallet of paper, for forming a new plurality of the paired transmitted and received microwaves associated with the different angular positions circumscribing around each same new volumetric segment, for each of a plurality of the new volumetric segments, thereby completing a three-dimensional microwave scan of at least a portion of the whole roll or pallet of paper; and (e) using a set of the pluralities of the paired transmitted and received microwaves associated with the different angular positions circumscribing around each of the volumetric segments of the roll or pallet of paper for the three-dimensional volumetric mapping of the internal properties and characteristics of the at least part of the whole roll or pallet of paper.

According to further characteristics in preferred embodiments of the invention described below, a set of the pluralities of the paired transmitted and received microwaves associated with the different angular positions circumscribing around each of the volumetric segments of the roll or pallet of paper is used for calculating values of internal properties and characteristics of at least part of the whole roll or pallet of paper.

According to further characteristics in preferred embodiments of the invention described below, a set of the pluralities of the paired transmitted and received microwaves associated with the different angular positions circumscribing around each of the volumetric segments of the roll or pallet of paper is used for three-dimensional volumetric mapping of internal properties and characteristics of at least part of the whole roll or pallet of paper.

According to further characteristics in preferred embodiments of the invention described below, the angular step size is constant.

According to further characteristics in preferred embodiments of the invention described below, the angular step size is variable.

According to further characteristics in preferred embodiments of the invention described below, the longitudinal step size is constant.

According to further characteristics in preferred embodiments of the invention described below, the longitudinal step size is variable.

According to further characteristics in preferred embodiments of the invention described below, the transmitted microwaves propagating within and through a portion of a volumetric segment are of a constant amplitude, with a constant frequency.

According to further characteristics in preferred embodiments of the invention described below, the transmitted microwaves propagating within and through a portion of a volumetric segment are of a constant amplitude, with a variable frequency.

According to further characteristics in preferred embodiments of the invention described below, the transmitted microwaves propagating within and through a portion of a volumetric segment are of a variable amplitude, with a variable frequency.

According to further characteristics in preferred embodiments of the invention described below, for the whole roll or pallet of paper whose individual cross-sectional volumetric segment has a total planar path length, through which the transmitted microwaves propagate, on order of about 1 meter (1000 centimeters), the transmitted microwaves have a frequency in a range of between about 1 GHz and about 5 GHz.

According to further characteristics in preferred embodiments of the invention described below, for the whole roll or pallet of paper whose individual cross-sectional volumetric segment has a total planar path length, through which the transmitted microwaves propagate, on order of about 0.1 meter (100 centimeters), the transmitted microwaves have a frequency in a range of between about 10 GHz and about 30 GHz.

The present invention can be implemented by performing procedures, steps, and sub-steps, in a manner selected from the group consisting of manually, semi-automatically, fully automatically, and a combination thereof, involving operation of system units, sub-units, devices, mechanisms, assemblies, structures, components, and elements, in a manner selected from the group consisting of manual, semi-automatic, fully automatic, and a combination thereof. Moreover, according to actual procedures, steps, sub-steps, system units, sub-units, devices, mechanisms, assemblies, structures, components, and elements, used for implementing a particular embodiment of the disclosed invention, the procedures, steps, and sub-steps, are performed by using hardware, software, or/and an integrated combination thereof, and the system units, sub-units, devices, mechanisms, assemblies, structures, components, and elements, operate by using hardware, software, or/and an integrated combination thereof.

In particular, software used for implementing the present invention includes operatively connected and functioning written or printed data, in the form of software programs, software routines, software sub-routines, software symbolic languages, software code, software instructions or protocols, or/and a combination thereof. Hardware used for implementing the present invention includes operatively connected and functioning electronic or/and electromechanical system units, sub-units, devices, mechanisms, assemblies, structures, components, and elements, including at least one computer chip, integrated circuit, electronic circuit, electronic sub-circuit, hard-wired electrical circuit, or/and a combination thereof, involving digital or/and analog operations. Accordingly, an integrated combination of (1) software and (2) hardware, used for implementing the present invention, includes an integrated combination of (1) operatively connected and functioning written or printed data, in the form of software programs, software routines, software sub-routines, software symbolic languages, software code, software instructions or protocols, or/and a combination thereof, and (2) operatively connected and functioning electronic or/and electromechanical system units, sub-units, devices, mechanisms, assemblies, structures, components, and elements, including at least one computer chip, integrated circuit, electronic circuit, electronic sub-circuit, hardwired electrical circuit, or/and a combination thereof, involving digital or/and analog operations.

BRIEF DESCRIPTION OF THE DRAWINGS

The present invention is herein described, by way of example only, with reference to the accompanying drawings. With specific reference now to the drawings in detail, it is stressed that the particulars shown are by way of example and for purposes of illustrative description of the preferred embodiments of the present invention only, and are presented in the cause of providing what is believed to be the most useful and readily understood description of the principles and conceptual aspects of the present invention. In this regard, no attempt is made to show structural details of the present invention in more detail than is necessary for a fundamental understanding of the invention, the description taken with the drawings making apparent to those skilled in the art how the several forms of the invention may be embodied in practice. In the drawings:

FIGS. 3a, 3b, and 3c are schematic diagrams illustrating an exemplary preferred embodiment of the method of the present invention, specifically implemented for bi-directional (longitudinal and angular) three-dimensional microwave scanning of a whole roll of paper, such as that illustrated in FIG. 1, in accordance with the present invention;

FIGS. 4a, 4b, and 4c are schematic diagrams illustrating an exemplary preferred embodiment of the method of the present invention, specifically implemented for bi-directional (longitudinal and angular) three-dimensional microwave scanning of a whole pallet of paper, such as that illustrated in FIG. 2, in accordance with the present invention;

DESCRIPTION OF THE PREFERRED EMBODIMENTS

Figure 1:
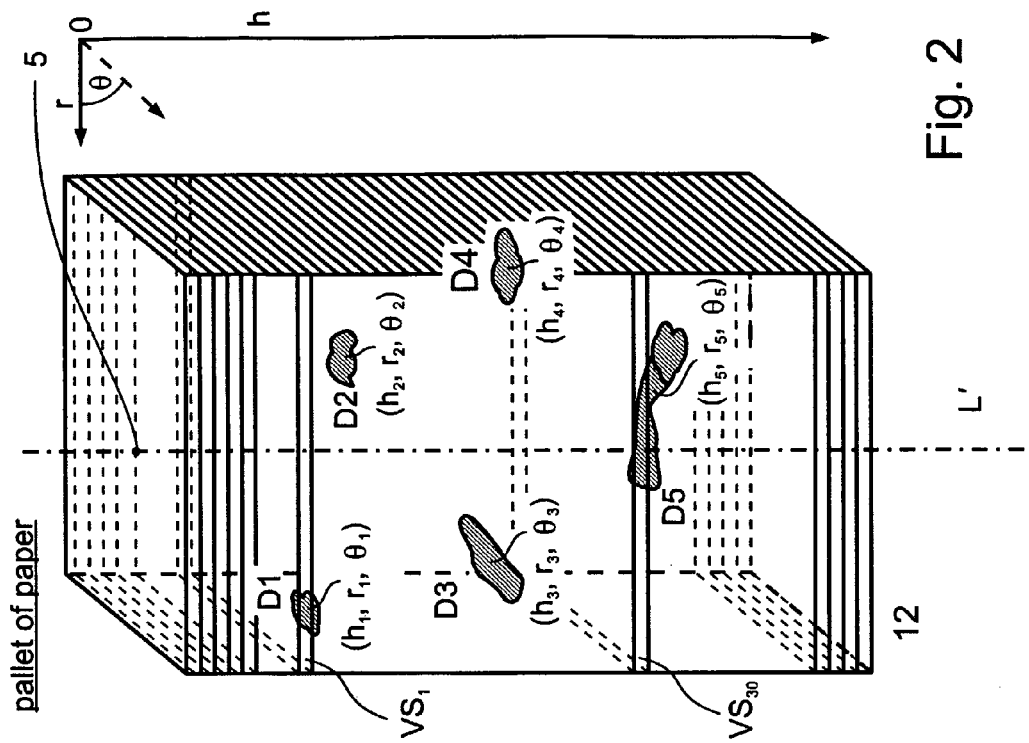
FIG. 1 is a schematic diagram illustrating a cylindrically shaped exemplary whole roll of paper, which can be subjected to the present invention, in accordance with the present invention.

The present invention relates to a method of bi-directional (longitudinal and angular) three-dimensional microwave scanning of a whole roll or pallet of paper. The method of the present invention enables, and further includes, three-dimensional volumetric mapping of internal properties and characteristics, such as moisture content, density, material uniformity, and, defects and types thereof, and variabilities thereof, of the whole roll or pallet of paper.

Microwaves, having one or more constant or/and variable amplitudes or/and frequencies, are transmitted into, and propagate through, longitudinally and angularly defined portions of individual cross-sectional volumetric (three-dimensional) segments of a whole roll or pallet of paper, such that the parameters (amplitude, phase) of the propagating microwaves are perturbed by, and are a function of the internal properties and characteristics of, the contents of the volumetric segment portions of the whole roll or pallet of paper. At least a portion of the propagating microwaves exiting the opposite side of each cross-sectional volumetric segment is received. The parameters (amplitude, phase) of both the transmitted microwaves and the received microwaves are used for calculating the microwave differential parameters of amplitude attenuation and phase shift, which in turn, are used for calculating and determining values, relationships, two-dimensional graphs and maps, and, three-dimensional volumetric graphs and maps, of the internal properties and characteristics, such as moisture content, density, material uniformity, and, defects and types thereof, and variabilities thereof, of at least part of the whole roll or pallet of paper.

'Test' values of the microwave differential parameters, amplitude attenuation and phase shift, are calculated by analyzing the transmitted and received microwaves. This data is compared to 'calibration' values of corresponding microwave differential parameters obtained from a similarly analyzed reference roll or pallet of paper having known internal properties and characteristics. The sets of test and calibration microwave differential parameter data, along with sophisticated software based automatic pattern recognition (APR) and classification data analysis techniques, are used for generating meaningful data and information, in particular, values, relationships, two-dimensional graphs and maps, and, three-dimensional volumetric graphs and maps, of the internal properties and characteristics, such as moisture content, density, material uniformity, and, defects and types thereof, and variabilities thereof, of at least part of the whole roll or pallet of paper.

The generated data and information characterizing the whole roll or pallet of paper are directly applicable for optimally designing, performing, validating, analyzing, monitoring, QC/QA testing, controlling, and troubleshooting, of an overall commercial paper or paper product manufacturing process, in a 'smart' (accurate, precise, and cost effective) manner.

For implementing each main aspect of the present invention, an exemplary microwave generating/transmitting/receiving/analyzing system, which includes a single robotic arms microwave generating/transmitting/receiving unit for holding, maneuvering, and (longitudinally and angularly) positioning, a single paired microwave transmitter and microwave receiver, is used as part of the automatic bi-directional (longitudinal and angular) three-dimensional microwave 'step-wise' scanning of cross-sectional volumetric segments of the whole roll or pallet of paper.

A first main aspect of the present invention is provision of a method of bi-directional (longitudinal and angular) three-dimensional microwave scanning of a whole roll or pallet of paper, which includes the following main steps: (a) transmitting microwaves into a portion of a cross-sectional volumetric segment of the whole roll or pallet of paper, wherein the cross-sectional volumetric segment lies in a plane perpendicular to, and is centered around a longitudinal position located along, longitudinal axis of the roll or pallet of paper, such that the transmitted microwaves propagate within and through the portion, for forming transmitted microwaves associated with the portion of the volumetric segment; (b) receiving at least a portion of the propagating microwaves exiting opposite side of the volumetric segment, for forming received microwaves associated with the portion of the volumetric segment; (c) repeating steps (a) and (b), at end of each of a plurality of angular step sizes circumscribing around the volumetric segment, for forming a plurality of paired transmitted and received microwaves associated with a respective plurality of new portions of the volumetric segment, such that the portion and the new portions of the volumetric segment are each associated with a different angular position circumscribing around the same volumetric segment; and (d) repeating steps (a) through (c), for a plurality of longitudinal step sizes longitudinally extending along the longitudinal axis of the roll or pallet of paper, wherein each step size is associated with a respective new cross-sectional volumetric segment lying in a plane perpendicular to, and centered around a new longitudinal position located along, the longitudinal axis of the roll or pallet of paper, for forming a new plurality of the paired transmitted and received microwaves associated with the different angular positions circumscribing around each same new volumetric segment, for each of a plurality of the new volumetric segments, thereby completing a three-dimensional microwave scan of at least a part of the whole roll or pallet of paper.

Following completion of performing the method of bi-directional (longitudinal and angular) three-dimensional microwave scanning of the whole roll or pallet of paper, a set of the pluralities of the paired transmitted and received microwaves associated with the different angular positions circumscribing around each of the volumetric segments of the roll or pallet of paper is used for three-dimensional volumetric mapping of internal properties and characteristics of the at least part of the whole roll or pallet of paper.

A second main aspect of the present invention is provision of a method of three-dimensional volumetric mapping of internal properties and characteristics of a whole roll or pallet of paper, which includes the following main steps: (a) transmitting microwaves into a portion of a cross-sectional volumetric segment of the whole roll or pallet of paper, wherein the cross-sectional volumetric segment lies in a plane perpendicular to, and is centered around a longitudinal position located along, longitudinal axis of the roll or pallet of paper, such that the transmitted microwaves propagate within and through the portion, for forming transmitted microwaves associated with the portion of the volumetric segment; (b) receiving at least a portion of the propagating microwaves exiting opposite side of the volumetric segment, for forming received microwaves associated with the portion of the volumetric segment; (c) repeating steps (a) and (b), at end of each of a plurality of angular step sizes circumscribing around the volumetric segment, for forming a plurality of paired transmitted and received microwaves associated with a respective plurality of new portions of the volumetric segment, such that the portion and the new portions of the volumetric segment are each associated with a different angular position circumscribing around the same volumetric segment; (d) repeating steps (a) through (c), for a plurality of longitudinal step sizes longitudinally extending along the longitudinal axis of the roll or pallet of paper, wherein each step size is associated with a respective new cross-sectional volumetric segment lying in a plane perpendicular to, and centered around a new longitudinal position located along, the longitudinal axis of the roll or pallet of paper, for forming a new plurality of the paired transmitted and received microwaves associated with the different angular positions circumscribing around each same new volumetric segment, for each of a plurality of the new volumetric segments, thereby completing a three-dimensional microwave scan of at least a part of the whole roll or pallet of paper; and (e) using a set of the pluralities of the paired transmitted and received microwaves associated with the different angular positions circumscribing around each of the volumetric segments of the roll or pallet of paper for the three-dimensional volumetric mapping of the internal properties and characteristics of the at least part of the whole roll or pallet of paper.

It is to be understood that the present invention is not limited in its application to the details of the order or sequence, and number, of procedures, steps, and sub-steps, of operation or implementation of the method, or to the details of type, composition, construction, arrangement, order, and number, of system units, sub-units, devices, mechanisms, assemblies, structures, components, elements, and materials, set forth in the following description and accompanying drawings, or examples.

For example, the following illustrative description refers to a cylindrically shaped exemplary whole roll of paper, and to a rectangularly shaped exemplary whole pallet of paper, and refers to a an exemplary microwave transmitting/receiving/analyzing system, which includes a single robotic arms unit for holding, maneuvering, and (longitudinally and angularly) positioning, a single paired microwave transmitter and microwave receiver, used as part of the automatic bi-directional (longitudinal and angular) three-dimensional microwave 'step-wise' scanning of cross-sectional volumetric segments of the cylindrically shaped whole roll of paper, or of the rectangularly shaped whole pallet of paper, in order to illustrate implementation of the present invention.

Additionally, for example, the following illustrative description is of a preferred embodiment wherein there is initial longitudinal positioning, and then step-wise longitudinally translating the paired microwave transmitter and microwave receiver, by a plurality of longitudinal step sizes along the longitudinal axis of the whole roll or pallet of paper, to a respective plurality of new longitudinal positions associated with a respective plurality of new cross-sectional volumetric segments of the roll or pallet of paper, and refers to initial angular positioning, and then step-wise angularly rotating the paired microwave transmitter and microwave receiver, by a plurality of angular step sizes circumscribing around each cross-sectional volumetric segment, to a respective plurality of new angular positions associated with a respective plurality of new portions of each cross-sectional volumetric segment of the roll or pallet of paper.

In general, the present invention can be implemented according to a variety of different alternative ways or/and according to a variety of different alternative embodiments.

For example, a first such alternative way or embodiment is wherein there is initial longitudinal positioning, and then step-wise longitudinally translating the whole roll or pallet of paper (instead of the paired microwave transmitter and microwave receiver), by a plurality of longitudinal step sizes along the longitudinal axis of the whole roll or pallet of paper, along with initial angular positioning, and then step-wise angularly rotating the whole roll or pallet of paper (instead of the paired microwave transmitter and microwave receiver), by a plurality of angular step sizes circumscribing around each cross-sectional volumetric segment of the roll or pallet of paper.

Alternatively, the present invention can be implemented in a way or embodiment corresponding to a combination of the above procedures. For example, in a way or embodiment wherein there is longitudinally positioning and translating the paired microwave transmitter and microwave receiver, followed by initial angular positioning, and then step-wise angularly rotating the whole roll or pallet of paper. Alternatively, for example, in a way or embodiment wherein there is longitudinally positioning and translating the whole roll or pallet of paper, followed by initial angular positioning, and then step-wise angularly rotating the paired microwave transmitter and microwave receiver.

Accordingly, the present invention is capable of other embodiments and of being practiced or carried out in various ways. Although procedures, steps, sub-steps, and system units, sub-units, devices, mechanisms, assemblies, structures, components, elements, and materials, similar or equivalent to those described herein can be used for practicing or testing the present invention, suitable procedures, steps, sub-steps, and system units, sub-units, devices, mechanisms, assemblies, structures, components, elements, and materials, are described herein.

It is also to be understood that unless otherwise defined, all technical and scientific words, terms, or/and phrases, used herein throughout the present disclosure have either the identical or similar meaning as commonly understood by one of ordinary skill in the art to which this invention belongs. Phraseology, terminology, and, notation, employed herein throughout the present disclosure are for the purpose of description and should not be regarded as limiting. Moreover, all technical and scientific words, terms, or/and phrases, introduced, defined, described, or/and exemplified, in the above Background section, are equally or similarly applicable in the illustrative description of the preferred embodiments, examples, and appended claims, of the present invention. Additionally, as used herein, the term 'about' refers to ±10% of the associated value.

Procedures, steps, sub-steps, system units, sub-units, devices, mechanisms, assemblies, structures, components, elements, materials, operation, implementation, of exemplary preferred embodiments, alternative preferred embodiments, specific configurations, and, additional and optional aspects, characteristics, or features, thereof, of the present invention, are better understood with reference to the following illustrative description and accompanying drawings. Throughout the following illustrative description and accompanying drawings, same reference numbers or/and letters refer to same system units, sub-units, devices, mechanisms, assemblies, structures, components, or elements.

In the following illustrative description of the present invention, included are main or principal procedures, steps, and sub-steps, and main or principal system units, sub-units, devices, mechanisms, assemblies, structures, components, elements, and materials, and functions thereof, needed for sufficiently understanding proper 'enabling' utilization and implementation of the disclosed invention. Accordingly, description of various possible required or/and optional preliminary, intermediate, minor, procedures, steps, sub-steps, system units, sub-units, devices, mechanisms, assemblies, structures, components, elements, or/and materials, or/and functions thereof, which are readily known by one of ordinary skill in the art, or/and which are available in the prior art and technical literature relating to application of microwave radiation technology for measuring and determining internal properties and characteristics, such as moisture content, density, material uniformity, and, defects and types thereof, and variabilities thereof, of a material, such as paper, and relating to principles and practice of microwave radiation transmission, propagation, and reception, are at most only briefly indicated herein.

Figure 2:
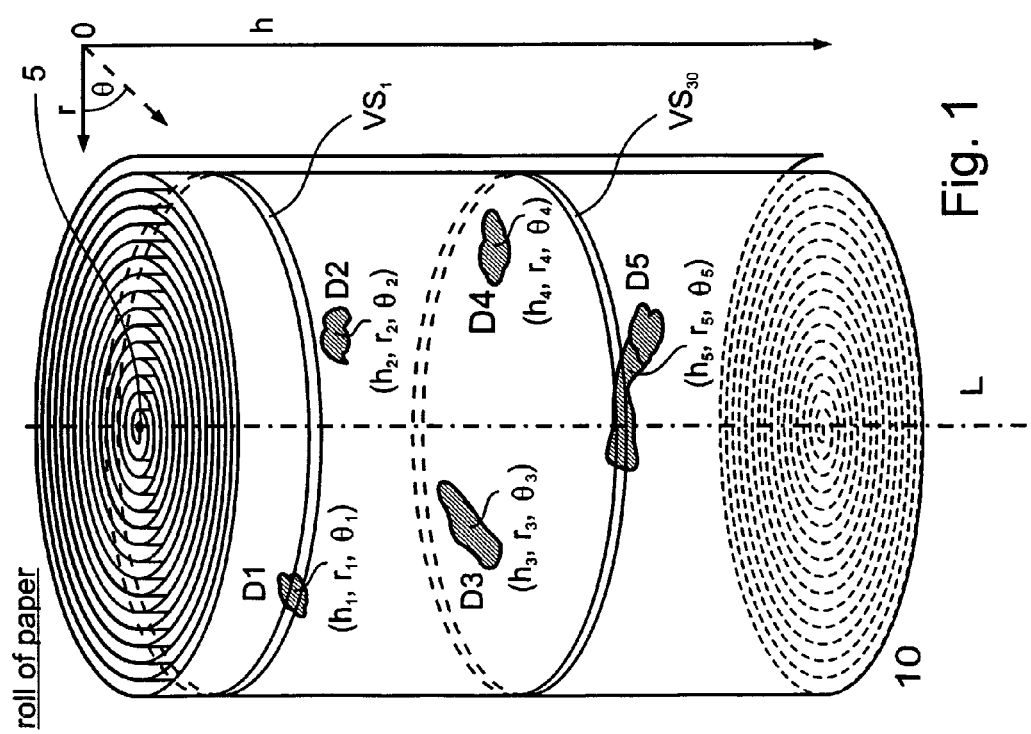
FIG. 2 is a schematic diagram illustrating a rectangularly shaped exemplary whole pallet of paper, which can be subjected to the present invention, in accordance with the present invention.

Reference is now made to FIGS. 1 and 2. FIG. 1 is a schematic diagram illustrating a cylindrically shaped exemplary whole roll 10 of paper, and FIG. 2 is a schematic diagram illustrating a rectangularly shaped exemplary whole pallet 12 of paper, each of which can be subjected to the present invention. As shown in FIG. 1, exemplary whole roll 10 of paper has a cylindrical shape whose longitudinal (length or height) axis is denoted by L, while in FIG. 2, exemplary whole pallet 12 of paper has a rectangular shape whose longitudinal (length or height) axis is denoted by L'. For clarity of illustration, while intending not to detract from the full meaning and understanding of the description of the present invention, in FIG. 1, part of rolls or coils of paper making up whole roll 10 of paper are explicitly shown only in the top and bottom ends of whole roll 10 of paper, and in FIG. 2, part of individual stacked sheets or pieces of paper making up whole pallet 12 of paper are explicitly shown only in the top, bottom, and single side, outer surfaces, of whole pallet 12 of paper. It is to be fully understood in the illustrative description of the present invention, that the partly illustrated rolls or coils of paper making up whole roll 10 of paper fully extend throughout the entire three-dimensional volume of whole roll 10 of paper, and that the partly illustrated individual stacked sheets or pieces of paper making up whole pallet 12 of paper fully extend throughout the entire three-dimensional volume of whole pallet 12 of paper.

In each of FIGS. 1 and 2, a reference three-dimensional cylindrical coordinate system 5, herein, referred to as reference coordinate system 5, having r (linear), $\theta$ (angular), and h (linear), coordinates, with an r-axis, an h-axis, and origin 0, is used for identifying and characterizing specific positions within the three-dimensional volume of each of whole roll 10 of paper or whole pallet 12 of paper, respectively. In reference coordinate system 5, for all values of r and $\theta$, the h-axis is to be understood as coinciding with the longitudinal axis (L or L') of whole roll 10 of paper or whole pallet 12 of paper, respectively, while for all values of h and $\theta$, the r-axis is to be understood as lying in a given plane perpendicular to the longitudinal axis (L or L') of whole roll 10 of paper or whole pallet 12 of paper, respectively.

Each of whole roll 10 of paper or whole pallet 12 of paper has a variety of different internal properties and characteristics, such as moisture content, density, material uniformity, and, defects and types thereof, and variabilities thereof. In a given whole roll 10 of paper or whole pallet 12 of paper, the internal properties and characteristics vary to a lesser or greater extent, relative to average values, throughout the volume of whole roll 10 of paper or whole pallet 12 of paper.

For illustrative purposes, in FIGS. 1 and 2, each of whole roll 10 of paper or whole pallet 12 of paper, respectively, is shown as having a plurality of exemplary anomalous or deviant three-dimensional regions, herein, referred to as D1, D2, D3, D4, and D5, located at various positions throughout the volume of whole roll 10 of paper or of whole pallet 12 of paper. For example, in terms of the r, θ, and h, coordinates of reference coordinate system 5, each anomalous or deviant region D1, D2, D3, D4, and D5 can be characterized as having a central, or center-of-gravity, position associated with a corresponding set of central, or center-of-gravity, coordinates, $(r_k, \theta_k, \text{ and } h_k)$, in particular, $(r_1, \theta_1, \text{ and } h_1)$, $(r_2, \theta_2, \text{ and } h_2)$, $(r_3, \theta_3, \text{ and } h_3)$, $(r_4, \theta_4, \text{ and } h_4)$, and $(r_5, \theta_5, \text{ and } h_5)$, respectively.

Each anomalous or deviant region D1, D2, D3, D4, and D5 is characterized by having anomalous or deviant values (higher or lower than average values) of at least one of the internal properties and characteristics of moisture content, density, material uniformity, and, defects and types thereof, and variabilities thereof, of whole roll 10 of paper or of whole pallet 12 of paper. Typically, anomalous or deviant regions D1, D2, D3, D4, and D5 arise as a result of the presence of non-uniformities or/and defects in the bulk wood pulp or/and wood chips used as raw materials for manufacturing whole roll 10 of paper or of whole pallet 12 of paper in the paper mill, or/and arise as a result of some anomaly or defect, for example, excess air or/and a foreign object, introduced during the manufacturing process.

A commercially manufactured whole roll 10 of paper or whole pallet 12 of paper having such anomalous or deviant regions D1, D2, D3, D4, or/and D5 may cause values of the internal properties and characteristics to be outside of acceptable ranges or/and may undesirably cause them to change prior to whole roll 10 of paper or whole pallet 12 of paper being sent to, or used in, the next manufacturing process. During or/and following such a manufacturing sequence, it is critically important that the internal properties and characteristics of whole roll 10 of paper or whole pallet 12 of paper be determined and monitored, such as by employing quality control and quality assurance procedures. Data and information obtained from the quality control and quality assurance procedures would then be used for controlling or/and adjusting the internal properties and characteristics of whole roll 10 of paper or whole pallet 12 of paper, such as by employing process control and process feedback procedures, prior to whole roll 10 of paper or whole pallet 12 of paper being sent to, or used in, the next manufacturing process or storage, in order to assure proper characteristics and performance of finished paper or finished paper products manufactured from whole roll 10 of paper or whole pallet 12 of paper.

In Step (a) of the method of bi-directional (longitudinal and angular) three-dimensional microwave scanning of a whole roll or pallet of paper, there is transmitting microwaves into a portion of a cross-sectional volumetric segment of the whole roll or pallet of paper, wherein the cross-sectional volumetric segment lies in a plane perpendicular to, and is centered around a longitudinal position located along, the longitudinal axis of the roll or pallet of paper, such that the transmitted microwaves propagate within and through the portion, for forming transmitted microwaves associated with the portion of the volumetric segment.

For implementing the present invention, whole roll 10 of paper (FIG. 1) or whole pallet 12 of paper (FIG. 2) is divided into, and characterized by, a plurality of individual cross-sectional volumetric (three-dimensional) segments, herein, each being referred to as a cross-sectional volumetric segment $VS_i$ (where the sub-i index represents the i-th longitudinal (or h-axis) position), extending along the longitudinal axis (L or L') of whole roll 10 of paper or whole pallet 12 of paper, respectively (and correspondingly, extending along the h-axis of reference coordinate system 5). For example, two cross-sectional volumetric segments, $VS_1$ and $VS_{30}$, are shown for each of whole roll 10 of paper and whole pallet 12 of paper. Each cross-sectional volumetric segment $VS_i$, for example, each cross-sectional volumetric segment $VS_1$ and $VS_{30}$, of whole roll 10 of paper or whole pallet 12 of paper, lies in a plane (defined by the r-axis and θ of reference coordinate system 5) perpendicular to the longitudinal axis (L or L') of whole roll 10 of paper or whole pallet 12 of paper, respectively, (and therefore, perpendicular to the h-axis of reference coordinate system 5) and each is centered around the i-th longitudinal position located along the longitudinal axis (L or L') of whole roll 10 of paper or whole pallet 12 of paper, respectively.

A given cross-sectional volumetric segment $VS_i$ may include at least part of one or more exemplary anomalous or deviant regions D1, D2, D3, D4, or/and D5 of the internal properties and characteristics of whole roll 10 of paper or whole pallet 12 of paper. For example, as shown in FIGS. 1 and 2, in each of whole roll 10 of paper and whole pallet 12 of paper, respectively, cross-sectional volumetric segment $VS_1$ includes part of anomalous or deviant region D1 whose central, or center-of-gravity, position is associated with central, or center-of-gravity, coordinates $(r_1, \theta_1, \text{ and } h_1)$, and cross-sectional volumetric segment $VS_{30}$ includes part of anomalous or deviant region D5 whose central, or center-of-gravity, position is associated with central, or center-of-gravity, coordinates $(r_5, \theta_5, \text{ and } h_5)$.

The longitudinal (length or height) dimension of, and therefore, volume of paper occupied by, each cross-sectional volumetric segment $VS_i$ are arbitrary, and are set primarily according to the total longitudinal (length or height) dimension, and internal properties and characteristics (such as moisture content, density, material uniformity, and, defects and types thereof, and variabilities thereof) of an actual whole roll 10 of paper or whole pallet 12 of paper subjected to the present invention, and according to structure, function, and, operating conditions and parameters (for example, speed, sensitivity, resolution) of a particular microwave transmitting/receiving/analyzing system, device, or apparatus, used for implementing the present invention. For example, for implementing the present invention in a manner resulting in high resolution, and therefore, in high accuracy, although, possibly at the expense of requiring relatively long overall analysis times, there is selecting the longitudinal (length or height) dimension of, and therefore, volume of paper occupied by, each cross-sectional volumetric segment $VS_i$, to be relatively small compared to the total longitudinal (length or height) dimension, and total volume of paper occupied by, whole roll 10 of paper or whole pallet 12 of paper subjected to the present invention.

Reference is now made to FIGS. 3a-3c, and FIGS. 4a-4c. FIGS. 3a-3c are schematic diagrams illustrating an exemplary preferred embodiment of the method of the present invention, specifically implemented for bi-directional (longitudinal and angular) three-dimensional microwave scanning of a whole roll of paper, such as exemplary whole roll 10 of paper illustratively described hereinabove with reference to FIG. 1. FIGS. 4a-4c are schematic diagrams illustrating an exemplary preferred embodiment of the method of the present invention, specifically implemented for bi-directional (longitudinal and angular) three-dimensional microwave scanning of a whole pallet of paper, such as exemplary whole pallet 12 of paper illustratively described hereinabove with reference to FIG. 2.

Similar to the above illustrative description of whole roll 10 of paper or whole pallet 12 of paper, in FIGS. 1 and 2, respectively, for clarity of illustration, while intending not to detract from the full meaning and understanding of the description of the present invention, in FIGS. 3a-3c, rolls or coils of paper making up whole roll 10 of paper are not explicitly shown, and in FIGS. 4a-4c, individual stacked sheets or pieces of paper making up whole pallet 12 of paper are not explicitly shown. Additionally, for clarity of illustration, in FIGS. 3a-3c and in FIGS. 4a-4c, exemplary anomalous or deviant three-dimensional regions D1, D2, D3, D4, and D5, located at various positions throughout the volume of each of whole roll 10 of paper or of whole pallet 12 of paper, are not explicitly shown, but are to be fully understood as being present, in particular, as they are explicitly shown in whole roll 10 of paper or whole pallet 12 of paper, in FIGS. 1 and 2, respectively. It is to be fully understood that for practicing the present invention, these forms of paper content and material, as well as anomalous or deviant regions, are clearly present in an actual whole roll of paper or in an actual whole pallet of paper.

In general, any of a wide variety of different types, configurations, and constructions, of microwave based systems, units, devices, apparatuses, mechanisms, assemblies, structures, components, elements, and materials, can be used for implementing the method of the present invention. Since the scope of the present invention is focused on methodology, as opposed to structure and function of equipment hardware, of bi-directional (longitudinal and angular) three-dimensional microwave scanning of a whole roll or pallet of paper, and of three-dimensional volumetric mapping of internal properties and characteristics, such as moisture content, density, material uniformity, and, defects and types thereof, and variabilities thereof, of the whole roll or pallet of paper, herein, there is illustratively described a relatively simple, but entirely enabled and functional, exemplary embodiment of a microwave based system that is suitable for implementing the present invention.

As shown in FIGS. 3a-3c, and in FIGS. 4a-4c, a microwave generating/transmitting/receiving/analyzing system, herein, generally referred to as microwave based system 20, is positioned relative to whole roll 10 of paper (FIGS. 3a-3c) or whole pallet 12 of paper (FIGS. 4a-4c), in a configuration wherein there is no 'physical' contact between any component of microwave based system 20 and whole roll 10 of paper or whole pallet 12 of paper. Microwave based system 20, and components thereof, are structured and function for enabling implementation and practice of the present invention. More specifically, for enabling implementation and practice of bidirectional (longitudinal and angular) three-dimensional microwave scanning of whole roll 10 of paper or whole pallet 12 of paper, and, in a non-limiting manner, for enabling implementation and practice of a main application of the present invention, being three-dimensional volumetric mapping of internal properties and characteristics, such as moisture content, density, material uniformity, and, defects and types thereof, and variabilities thereof, of whole roll 10 of paper or whole pallet 12 of paper.

Microwave based system 20 includes as main components: a robotic arms microwave generating/transmitting/receiving unit 22, and a process control and data analysis unit 24. Optionally, microwave based system 20 further includes an operator workstation unit 26.

Robotic arms microwave generating/transmitting/receiving unit 22, herein, equivalently and generally referred to as robotic arms microwave unit 22, is for (longitudinally and angularly) holding, maneuvering, and positioning, a mounted paired microwave transmitter $T_{i,j}$ and microwave receiver $R_{i,j}$, relative to longitudinal axis L of whole roll 10 of paper (FIGS. 3a-3c) or relative to longitudinal axis L' of whole pallet 12 of paper (FIGS. 4a-4c). The sub-i index represents the i-th longitudinal (or h-axis) position, and the sub-j index represents the j-th angular (or θ) position (in terms of angular step size α [as particularly shown, for example, in upper portions of FIGS. 3a and 4a]), of paired microwave transmitter $T_{ij}$ relative to the longitudinal axis (L or L') of whole roll 10 of paper (FIGS. 3a-3c) or of whole pallet 12 of paper (FIGS. 4a-4c), where microwave receiver $R_{ij}$ is assigned the same sub-i longitudinal and sub-j angular position indices as microwave transmitter $T_{ij}$.

Regarding use and understanding of the sub-i index, herein, sub-i index of the i-th longitudinal position of paired microwave transmitter $T_{ij}$ and microwave receiver $R_{ij}$ relative to the longitudinal axis (L or L') of whole roll 10 of paper (FIGS. 3a-3c) or of whole pallet 12 of paper (FIGS. 4a-4c) correspond to the same sub-i index of the hereinabove illustratively described i-th longitudinal position of a cross-sectional volumetric segment $VS_i$ extending along the longitudinal axis (L or L') of whole roll 10 of paper or whole pallet 12 of paper.

Robotic arms microwave unit 22 includes as main components: mounted and paired microwave transmitter $T_{ij}$ and microwave receiver $R_{ij}$; a robotic arms assembly 28; a robotic arms assembly moving and positioning mechanism 30; a robotic arms assembly first longitudinal extending mechanism 32; and a robotic arms assembly second longitudinal extending mechanism 34.

Microwave transmitter $T_{ij}$ is operatively mounted and connected to below the elbow of the first side arm of robotic arms assembly 28. Microwave transmitter $T_{ij}$ is a microwave based device or mechanism of appropriate structure and functioning for generating and transmitting microwaves (indicated in FIGS. 3a-3c, and in FIGS. 4a-4c, by the set of three small arrows extending from one of the sides of each microwave transmitter $T_{ij}$), having one or more constant or/and variable amplitudes or/and frequencies, into longitudinally and angularly defined portions of individual cross-sectional volumetric (three-dimensional) segments $VS_i$ extending along the longitudinal axis (L or L') of whole roll 10 of paper or whole pallet 12 of paper, such that the parameters (amplitude, phase) of the propagating microwaves are perturbed by, and are a function of the internal properties and characteristics of, the contents of the volumetric segment portions of whole roll 10 of paper or whole pallet 12 of paper.

Microwave receiver $R_{ij}$ is operatively mounted and connected to below the elbow of the second side arm of robotic arms assembly 28. Microwave receiver $R_{ij}$ is a microwave based device or mechanism of appropriate structure and functioning for receiving at least a portion of the propagating microwaves (indicated in FIGS. 3a-3c, and in FIGS. 4a-4c, by the set of three small arrows entering into one of the sides of each microwave receiver $R_{ij}$) exiting the opposite side of the corresponding individual cross-sectional volumetric (three-dimensional) segment $VS_i$ of whole roll 10 of paper or whole pallet 12 of paper.

Paired microwave transmitter $T_{ij}$ and microwave receiver $R_{ij}$ are capable of generating, transmitting, and receiving, microwaves having frequencies, f, in essentially the entire dynamic range of frequencies of microwave radiation.

Robotic arms assembly 28 is operatively connected to mounted paired microwave transmitter $T_{ij}$ and microwave receiver $R_{ij}$. Robotic arms assembly 28 is for firmly supporting and holding mounted paired microwave transmitter $T_{ij}$ and microwave receiver $R_{ij}$, as part of robotic arms microwave unit 22 functioning for maneuvering and (longitudinally and angularly) positioning paired microwave transmitter $T_{ij}$ and microwave receiver $R_{ij}$ relative to longitudinal axis L of whole roll 10 of paper or relative to longitudinal axis L' of whole pallet 12 of paper. Accordingly, robotic arms assembly 28 is longitudinally movable along, and angularly movable around, the longitudinal axis (L or L') of whole roll 10 of paper or whole pallet 12 of paper. Longitudinal moving and positioning of robotic arms assembly 28 (indicated in FIGS. 3a-3c, and in FIGS. 4a-4c, by the paired arrows located adjacent to the outermost side of each 'elbow' of robotic arms assembly 28), and, angular moving (in terms of angular step size α) and positioning of robotic arms assembly 28 (indicated in FIGS. 3a-3c, and in FIGS. 4a-4c, by the circular arrow circling around the uppermost portion of the longitudinal axis (L or L') of whole roll 10 of paper or whole pallet 12 of paper), are effected or actuated by robotic arms assembly moving and positioning mechanism 30.

Robotic arms assembly moving and positioning mechanism 30 is operatively connected to (the center of) robotic arms assembly 28. Robotic arms assembly moving and positioning mechanism 30 is for automatically effecting or actuating the longitudinal moving and positioning, and, the angular moving and positioning, of robotic arms assembly 28, along and around, respectively, the longitudinal axis (L or L') of whole roll 10 of paper or whole pallet 12 of paper. Accordingly, robotic arms assembly moving and positioning mechanism 30 automatically effects or actuates the longitudinal moving and positioning, and, the angular moving and positioning, of paired microwave transmitter $T_{ij}$ and microwave receiver $R_{ij}$, along and around, respectively, the longitudinal axis (L or L') of whole roll 10 of paper or whole pallet 12 of paper.

Robotic arms assembly first longitudinal extending mechanism 32 is operatively connected to below the elbow of the first side arm of robotic arms assembly 28 to which is operatively connected paired microwave transmitter $T_{ij}$. Robotic arms assembly second longitudinal extending mechanism 34 is operatively connected to below the elbow of the second side arm of robotic arms assembly 28 to which is operatively connected paired microwave receiver $R_{ij}$. Robotic arms assembly first and second longitudinal extending mechanisms 32 and 34, respectively, are, in addition to robotic arms assembly moving and positioning mechanism 30, for automatically effecting or actuating the longitudinal moving and positioning of paired microwave transmitter $T_{ij}$ and microwave receiver $R_{ij}$, respectively, along the longitudinal axis (L or L') of whole roll 10 of paper or whole pallet 12 of paper. Operations of robotic arms assembly first and second longitudinal extending mechanisms 32 and 34, respectively, are especially useful for implementing the present invention for relatively large magnitudes of the total longitudinal (length or height) dimension of whole roll 10 of paper or of whole pallet 12 of paper.

Microwave based system 20, in general, and robotic arms microwave unit 22, including robotic arms assembly 28, robotic arms assembly moving and positioning mechanism 30, as well as robotic arms assembly first and second longitudinal extending mechanisms 32 and 34, respectively, in particular, are structured, function, and operate, in a manner such that microwave receiver $R_{ij}$ and microwave transmitter $T_{ij}$, each positioned at a given i-th longitudinal position along the longitudinal axis (L or L') of whole roll 10 of paper or whole pallet 12 of paper, are substantially parallel to each other, in a manner such that at least a portion of the microwaves generated and transmitted by microwave transmitter $T_{ij}$ into the i-th longitudinally and angularly defined portion of a given individual cross-sectional volumetric segment $VS_i$ of whole roll 10 of paper or whole pallet 12 of paper, and which exit the opposite side of individual cross-sectional volumetric segment $VS_i$, are readily received by microwave receiver $R_{ij}$.

Process control and data analysis unit 24, of microwave based system 20, is operatively (in particular, electronically) connected to robotic arm microwave unit 22, and components thereof, for example, via robotic arms assembly moving and positioning mechanism 30. Process control and data analysis unit 24 is for overall automatically controlling robotic arms microwave unit 22, including robotic arms assembly 28, robotic arms assembly moving and positioning mechanism 30, as well as robotic arms assembly first and second longitudinal extending mechanisms 32 and 34, respectively. This includes controlling the (longitudinally and angularly) holding, maneuvering, and positioning, paired microwave transmitter $T_{ij}$ and microwave receiver $R_{ij}$, relative to longitudinal axis L of whole roll 10 of paper (FIGS. 3a-3c) or relative to longitudinal axis L' of whole pallet 12 of paper (FIGS. 4a-4c). This also includes controlling the generating and transmitting of microwaves by microwave transmitter $T_{ij}$, and controlling the receiving of the transmitted and propagated microwaves by microwave receiver $R_{ij}$.

Process control and data analysis unit 24 is also for processing and analyzing data and information generated during overall operation of microwave based system 20, during implementation of the present invention. This includes analyzing the transmitted and received microwaves for the purpose of calculating test values of the microwave differential parameters, amplitude attenuation and phase shift, and comparing the test values to calibration values of corresponding microwave differential parameters obtained from a similarly analyzed reference roll or pallet of paper having known internal properties and characteristics. Process control and data analysis unit 24 contains sophisticated software based automatic pattern recognition (APR) and classification data analysis techniques which are applied to sets of test and calibration microwave differential parameter data, for generating meaningful data and information, in particular, values, relationships, two-dimensional graphs and maps, and, three-dimensional volumetric graphs and maps, of the internal properties and characteristics, such as moisture content, density, material uniformity, and, defects and types thereof, and variabilities thereof, of at least part of whole roll 10 of paper or whole pallet 12 of paper.

Optional operator workstation unit 26, of microwave based system 20, is operatively connected to process control and data analysis unit 24. Operator workstation unit 26 includes, for example, a computerized operator workstation, for enabling an operator to send operating commands, instructions, and data, to process control and data analysis unit 24, as well as to receive data and information from process control and data analysis unit 24, during implementation of all aspects of the present invention.

In general, the parameters (amplitudes, frequencies) of the microwaves generated and transmitted by microwave transmitter $T_{ij}$ are selected primarily according to the total (r-θ) planar path length (perpendicular to the longitudinal axis (L or L') of whole roll 10 of paper or whole pallet 12 of paper, respectively) of the individual cross-sectional volumetric segments $VS_i$ through which the transmitted microwaves propagate and exit. The total (r-θ) planar path length (perpendicular to the longitudinal axis (L or L') of whole roll 10 of paper or whole pallet 12 of paper, respectively) of the individual cross-sectional volumetric segments $VS_i$ through which the transmitted microwaves propagate and exit, ordinarily corresponds to the total diameter of whole roll 10 of paper, or to the total width of whole pallet 12 of paper.

The parameters (amplitudes, frequencies) of the microwaves generated and transmitted by microwave transmitter $T_{ij}$ are also selected according to the internal properties and characteristics (such as moisture content, density, material uniformity, and, defects and types thereof, and variabilities thereof) of an actual whole roll 10 of paper or whole pallet 12 of paper subjected to the present invention, and, according to the operating conditions and parameters (for example, speed, sensitivity, resolution) of microwave based system 20, and components thereof, used for implementing the present invention.

As previously stated hereinabove, paired microwave transmitter $T_{ij}$ and microwave receiver $R_{ij}$ are capable of generating, transmitting, and receiving, microwaves having frequencies in essentially the entire dynamic range of frequencies of microwave radiation. Preferably, for whole roll 10 of paper or whole pallet 12 of paper whose individual cross-sectional volumetric segments $VS_i$ have a total (r-θ) planar path length, through which the transmitted microwaves propagate and exit, on the order of about 1 meter (100 centimeters), then microwaves having a frequency in a range of between about 1 GHz and about 5 GHz are used for implementing the present invention. Alternatively, for whole roll 10 of paper or whole pallet 12 of paper whose individual cross-sectional volumetric segments $VS_i$ have a total (r-θ) planar path length, through which the transmitted microwaves propagate, on the order of about 0.1 meter (10 centimeters), then microwaves having a frequency in a range of between about 10 GHz and about 30 GHz are used for implementing the present invention.

Accordingly, by using microwave based system 20, and components thereof, in Step (a), of the present invention, with reference to FIGS. 3a and 4a, there is transmitting microwaves into a portion of cross-sectional volumetric segment $VS_i$, for example, cross-sectional volumetric segment $VS_1$, of whole roll 10 of paper or whole pallet 12 of paper, wherein cross-sectional volumetric segment $VS_1$ lies in a plane perpendicular to, and is centered around a longitudinal position located along, the longitudinal axis (L or L') of whole roll 10 of paper or whole pallet 12 of paper, respectively, such that the transmitted microwaves propagate within and through the portion, for forming transmitted microwaves associated with the portion of cross-sectional volumetric segment $VS_1$.

As shown in each of FIGS. 3a and 4a, microwave based system 20, in general, and robotic arms microwave unit 22, including robotic arms assembly 28, robotic arms assembly moving and positioning mechanism 30, as well as robotic arms assembly first and second longitudinal extending mechanisms 32 and 34, respectively, in particular, are operated for longitudinally and angularly (rotationally) maneuvering, and positioning, paired microwave transmitter $T_{1,0}$ and microwave receiver $R_{1,0}$ relative to the longitudinal axis (L or L') of whole roll 10 of paper or of whole pallet 12 of paper, in a manner such that microwave transmitter $T_{1,0}$ transmits microwaves into a portion of cross-sectional volumetric segment $VS_1$.

Microwave transmitter $T_{1,0}$ transmits microwaves into the portion of cross-sectional volumetric segment $VS_1$ at an arbitrarily assigned initial angular position, in particular, corresponding to the zero (0-th) angular step of rotation (or θ position), having an angular step size α, of an exemplary sixteen (16) angular steps circling around whole roll 10 of paper or around whole pallet 12 of paper.

In Step (b), there is receiving at least a portion of the propagating microwaves exiting the opposite side of the volumetric segment, for forming received microwaves associated with the portion of the volumetric segment.

Accordingly, with reference to FIGS. 3a and 4a, simultaneous to Step (a), in Step (b), there is receiving at least a portion of the propagating microwaves exiting the opposite side of cross-sectional volumetric segment $VS_1$ at the zero (0-th) angular step of rotation (θ position), by microwave receiver $R_{1,0}$, for forming received microwaves associated with the portion of cross-sectional volumetric segment $VS_1$ at the zero (0-th) angular step of rotation (θ position).

The bottom part of each of FIGS. 3a and 4a shows a simple schematic overhead view of the just described scenario of performing Steps (a) and (b), for longitudinally and angularly (rotationally) scanning the zeroth (0-th) angular step of rotation (θ position) of cross-sectional volumetric segment $VS_1$ relative to the longitudinal axis (L or L') of whole roll 10 of paper or of whole pallet 12 of paper.

In Step (c), there is repeating Steps (a) and (b), at the end of each of a plurality of angular step sizes circumscribing around the cross-sectional volumetric segment, for forming a plurality of paired transmitted and received microwaves associated with a respective plurality of new portions of the cross-sectional volumetric segment, such that the portion and the new portions of the cross-sectional volumetric segment are each associated with a different angular position circumscribing around the same cross-sectional volumetric segment.

Accordingly, with reference to FIGS. 3b-3c, and 4b-4c, in Step (c), there is repeating Steps (a) and (b), at the end of each of a plurality of angular step sizes α, circumscribing around cross-sectional volumetric segment $VS_1$, for forming a plurality of paired transmitted and received microwaves associated with a respective plurality of new portions of cross-sectional volumetric segment $VS_1$, such that the portion and the new portions of cross-sectional volumetric segment $VS_1$ are each associated with a different angular (θ) position, for example, the third (3-rd) angular (θ) position (FIGS. 3b and 4b) and the sixth (6-th) angular (θ) position (FIGS. 3c and 4c), circumscribing around the same cross-sectional volumetric segment $VS_1$ of whole roll 10 of paper or of whole pallet 12 of paper.

For example, as shown in each of FIGS. 3b and 4b, microwave based system 20, in general, and robotic arms microwave unit 22, including robotic arms assembly 28, robotic arms assembly moving and positioning mechanism 30, as well as robotic arms assembly first and second longitudinal extending mechanisms 32 and 34, respectively, in particular, are operated for longitudinally and angularly (rotationally) maneuvering, and positioning, paired microwave transmitter $T_{1,0}$ and microwave receiver $R_{1,0}$ relative to the longitudinal axis (L or L') of whole roll 10 of paper or of whole pallet 12 of paper, along the same first (1-st) longitudinal (or h-axis) position, from the zeroth (0-th) angular step of rotation (θ) position, via three angular step sizes α, to the third (3-rd) angular step of rotation (θ) position, in a manner such that microwave transmitter $T_{1,3}$ transmits microwaves into a new portion circumscribing around the same cross-sectional volumetric segment $VS_1$ of whole roll 10 of paper or around whole pallet 12 of paper. Simultaneously, there is receiving at least a portion of the propagating microwaves exiting the opposite side of cross-sectional volumetric segment $VS_1$ at the third (3-rd) angular step of rotation (θ position), by microwave receiver $R_{1,3}$, for forming received microwaves associated with the new portion of cross-sectional volumetric segment $VS_1$ at the third (3-rd) angular step of rotation (θ position).

The bottom part of each of FIGS. 3b and 4b shows a simple schematic overhead view of the just described scenario of performing Steps (a) and (b), for longitudinally and angularly (rotationally) scanning the third (3-rd) angular step of rotation (θ position) of cross-sectional volumetric segment $VS_1$ relative to the longitudinal axis (L or L') of whole roll 10 of paper or of whole pallet 12 of paper.

By further repeating Steps (a) and (b), for example, as shown in each of FIGS. 3c and 4c, microwave based system 20, and components thereof, are operated for longitudinally and angularly (rotationally) maneuvering, and positioning, paired microwave transmitter $T_{1,3}$ and microwave receiver $R_{1,3}$ relative to the longitudinal axis (L or L') of whole roll 10 of paper or of whole pallet 12 of paper, along the same first (1-st) longitudinal (or h-axis) position, from the third (3-rd) angular step of rotation (θ) position, via three angular step sizes α, to the sixth (6-th) angular step of rotation (θ) position, in a manner such that microwave transmitter $T_{1,6}$ transmits microwaves into a new portion circumscribing around the same cross-sectional volumetric segment $VS_1$ of whole roll 10 of paper or around whole pallet 12 of paper. Simultaneously, there is receiving at least a portion of the propagating microwaves exiting the opposite side of cross-sectional volumetric segment $VS_1$ at the sixth (6-th) angular step of rotation (θ position), by microwave receiver $R_{1,6}$, for forming received microwaves associated with the new portion of cross-sectional volumetric segment $VS_1$ at the sixth (6-th) angular step of rotation (θ position).

The bottom part of each of FIGS. 3c and 4c shows a simple schematic overhead view of the just described scenario of performing Steps (a) and (b), for longitudinally and angularly (rotationally) scanning the sixth (6-th) angular step of rotation (θ position) of cross-sectional volumetric segment $VS_1$ relative to the longitudinal axis (L or L') of whole roll 10 of paper or of whole pallet 12 of paper.

In Step (d), there is repeating steps (a) through (c), for a plurality of longitudinal step sizes longitudinally extending along the longitudinal axis of the roll or pallet of paper, wherein each step size is associated with a respective new cross-sectional volumetric segment lying in a plane perpendicular to, and centered around a new longitudinal position located along, the longitudinal axis of the roll or pallet of paper, for forming a new plurality of the paired transmitted and received microwaves associated with the different angular positions circumscribing around each same new volumetric segment, for each of a plurality of the new volumetric segments, thereby completing a three-dimensional (volumetric) microwave scan of at least a part of the whole roll or pallet of paper.

Accordingly, with reference to FIGS. 3a-3c, and 4a-4c, in Step (d), there is repeating Steps (a) through (c), for a plurality of longitudinal step sizes longitudinally extending along the longitudinal axis (L or L') of whole roll 10 of paper or of whole pallet 12 of paper, corresponding to a plurality of longitudinal step sizes longitudinally extending along the h-axis of whole roll 10 of paper or of whole pallet 12 of paper, as shown in FIGS. 1 and 2, respectively. Each longitudinal step size is associated with a respective new cross-sectional volumetric segment $VS_i$ lying in a plane perpendicular to, and centered around a new i-th longitudinal (or h-axis) position located along, the longitudinal axis (L or L') of whole roll 10 of paper or of whole pallet 12 of paper, for forming a new plurality of the paired transmitted and received microwaves associated with the different angular steps of rotation (θ positions) circumscribing around each same new volumetric segment $VS_i$, for each of a plurality of the new volumetric segments $VS_i$, thereby completing a three-dimensional (volumetric) microwave scan of at least a part of whole roll 10 of paper or of whole pallet 12 of paper.

For example, as shown in each of FIGS. 3a and 4a, microwave based system 20, and components thereof, are operated for longitudinally and angularly (rotationally) maneuvering, and positioning, paired microwave transmitter $T_{1,0}$ and microwave receiver $R_{1,0}$ relative to the longitudinal axis (L or L') of whole roll 10 of paper or of whole pallet 12 of paper, from the 1st longitudinal (or h-axis) position, at the same zeroth (0-th) angular step of rotation (θ) position, via a plurality of longitudinal step sizes longitudinally extending along the longitudinal axis (L or L') to the thirtieth (30-th) longitudinal (or h-axis) position, in a manner such that microwave transmitter $T_{30,0}$ transmits microwaves into a portion of cross-sectional volumetric segment $VS_{30}$ of whole roll 10 of paper or around whole pallet 12 of paper. Simultaneously, there is receiving at least a portion of the propagating microwaves exiting the opposite side of cross-sectional volumetric segment $VS_{30}$ at the zeroth (0-th) angular step of rotation (θ position), by microwave receiver $R_{30,0}$, for forming received microwaves associated with the portion of the new cross-sectional volumetric segment $VS_{30}$ at the zeroth (0-th) angular step of rotation (θ position).

The bottom part of each of FIGS. 3a and 4a shows a simple schematic overhead view of the just described scenario of repeating Steps (a) and (b), as part of performing Step (d), for longitudinally and angularly (rotationally) scanning the zeroth (0-th) angular step of rotation (θ position) of cross-sectional volumetric segment $VS_{30}$ relative to the longitudinal axis (L or L') of whole roll 10 of paper or of whole pallet 12 of paper.

Accordingly, with reference to FIGS. 3b-3c, and 4b-4c, in Step (d), by repeating Step (c), there is repeating Steps (a) and (b), at the end of each of a plurality of angular step sizes α, circumscribing around cross-sectional volumetric segment $VS_{30}$, for forming a plurality of paired transmitted and received microwaves associated with a respective plurality of new portions of cross-sectional volumetric segment $VS_{30}$, such that the portion and the new portions of cross-sectional volumetric segment $VS_{30}$ are each associated with a different angular (θ) position, for example, the third (3-rd) angular (θ) position (FIGS. 3b and 4b) and the sixth (6-th) angular (θ) position (FIGS. 3c and 4c), circumscribing around the same cross-sectional volumetric segment $VS_{30}$ of whole roll 10 of paper or of whole pallet 12 of paper.

For example, as shown in each of FIGS. 3b and 4b, microwave based system 20, and components thereof, are operated for longitudinally and angularly (rotationally) maneuvering, and positioning, paired microwave transmitter $T_{30,0}$ and microwave receiver $R_{30,0}$ relative to the longitudinal axis (L or L') of whole roll 10 of paper or of whole pallet 12 of paper, along the same thirtieth (30-th) longitudinal (or h-axis) position, from the zeroth (0-th) angular step of rotation ($\theta$) position, via three angular step sizes $\alpha$, to the third (3-rd) angular step of rotation ($\theta$) position, in a manner such that microwave transmitter $T_{30,3}$ transmits microwaves into a new portion circumscribing around the same cross-sectional volumetric segment $VS_{30}$ of whole roll 10 of paper or around whole pallet 12 of paper. Simultaneously, there is receiving at least a portion of the propagating microwaves exiting the opposite side of cross-sectional volumetric segment $VS_{30}$ at the third (3-rd) angular step of rotation ($\theta$ position), by microwave receiver $R_{30},3$, for forming received microwaves associated with the new portion of cross-sectional volumetric segment $VS_{30}$ at the third (3-rd) angular step of rotation ($\theta$ position).

The bottom part of each of FIGS. 3b and 4b shows a simple schematic overhead view of the just described scenario of repeating Steps (a) and (b), as part of performing Step (d), for longitudinally and angularly (rotationally) scanning the third (3-rd) angular step of rotation ($\theta$ position) of cross-sectional volumetric segment $VS_{30}$ relative to the longitudinal axis (L or L') of whole roll 10 of paper or of whole pallet 12 of paper.

By further repeating Steps (a) and (b), as part of performing Step (d), for example, as shown in each of FIGS. 3c and 4c, microwave based system 20, and components thereof, are operated for longitudinally and angularly (rotationally) maneuvering, and positioning, paired microwave transmitter $T_{30,3}$ and microwave receiver $R_{30,3}$ relative to the longitudinal axis (L or L') of whole roll 10 of paper or of whole pallet 12 of paper, along the same thirtieth (30-th) longitudinal (or h-axis) position, from the third (3-rd) angular step of rotation ($\theta$) position, via three angular step sizes $\alpha$, to the sixth (6-th) angular step of rotation ($\theta$) position, in a manner such that microwave transmitter $T_{30,6}$ transmits microwaves into a new portion circumscribing around the same cross-sectional volumetric segment $VS_{30}$ of whole roll 10 of paper or around whole pallet 12 of paper. Simultaneously, there is receiving at least a portion of the propagating microwaves exiting the opposite side of cross-sectional volumetric segment $VS_{30}$ at the sixth (6-th) angular step of rotation ($\theta$ position), by microwave receiver $R_{30,6}$, for forming received microwaves associated with the new portion of cross-sectional volumetric segment $VS_{30}$ at the sixth (6-th) angular step of rotation ($\theta$ position).

The bottom part of each of FIGS. 3c and 4c shows a simple schematic overhead view of the just described scenario of repeating Steps (a) and (b), as part of performing Step (d), for longitudinally and angularly (rotationally) scanning the sixth (6-th) angular step of rotation ($\theta$ position) of cross-sectional volumetric segment $VS_{30}$ relative to the longitudinal axis (L or L') of whole roll 10 of paper or of whole pallet 12 of paper.

By performing Step (d), there is completing a three-dimensional (volumetric) microwave scan of at least a part of whole roll 10 of paper or of whole pallet 12 of paper.

Implementation of the above illustratively described method of bidirectional (longitudinal and angular) three-dimensional microwave scanning of whole roll 10 of paper or of whole pallet 12 of paper, relative to the longitudinal axis (L or L') of whole roll 10 of paper or of whole pallet 12 of paper, is done in any of a wide variety of different ways with respect to constancy or/and variation of the microwave signal parameters, amplitude and frequency (f), and with respect to constancy or/and variation of the bi-directional (longitudinal and angular (rotational)) scanning of whole roll 10 of paper or of whole pallet 12 of paper.

In particular, the present invention can be implemented by using a pre-determined constant or variable number of angular steps, for example, sixteen (16) angular steps, as illustratively described hereinabove, at a pre-determined constant or variable angular step size $\alpha$, for example, a constant angular step size $\alpha$ of 22.5° (corresponding to sixteen (16) equally sized angular steps), circumscribing around whole roll 10 of paper or of whole pallet 12 of paper, along with using a pre-determined constant or variable longitudinal step size incrementally extending along the longitudinal axis (L or L') of whole roll 10 of paper or whole pallet 12 of paper.

According to a specific preferred embodiment of the method of the present invention, the bi-directional (longitudinal and angular) three-dimensional microwave scanning of whole roll 10 of paper or of whole pallet 12 of paper, relative to the longitudinal axis (L or L') of whole roll 10 of paper or of whole pallet 12 of paper, is performed with microwave based system 20, and components thereof, operating at constant microwave amplitude, with a constant microwave frequency (f).

According to another specific preferred embodiment of the method of the present invention, the bi-directional (longitudinal and angular) three-dimensional microwave scanning of whole roll 10 of paper or of whole pallet 12 of paper, relative to the longitudinal axis (L or L') of whole roll 10 of paper or of whole pallet 12 of paper, is performed with microwave based system 20, and components thereof, operating at a constant microwave amplitude, with a variable microwave frequency (f).

According to another specific preferred embodiment of the method of the present invention, the bidirectional (longitudinal and angular) three-dimensional microwave scanning of whole roll 10 of paper or of whole pallet 12 of paper, relative to the longitudinal axis (L or L') of whole roll 10 of paper or of whole pallet 12 of paper, is performed with microwave based system 20, and components thereof, operating at variable microwave amplitudes, with a variable microwave frequency (f).

The immediately preceding two specific preferred embodiments of the method of the present invention can be implemented, for example, by using a 'frequency hopping' type of variable microwave frequency, as described in same Applicant's U.S. Pat. Nos. 6,107,809, and 6,025,724. Implementation of such specific preferred embodiments of the method of the present invention leads to obtaining high resolution, and therefore, high accuracy, of the results. Moreover, by implementing such specific preferred embodiments of the method of the present invention, the automatic pattern recognition (APR) and classification data analysis techniques, which are used for generating meaningful data and information, in particular, values, relationships, two-dimensional graphs and maps, and, three-dimensional volumetric graphs and maps, of the internal properties and characteristics, such as moisture content, density, material uniformity, and, defects and types thereof, and variabilities thereof, of at least part of whole roll 10 of paper or of whole pallet 12 of paper, are based on microwave data obtained at a multiple of frequencies (f).

By implementing the hereinabove illustrative described method of the present invention, microwaves, having one or more constant or/and variable amplitudes or/and frequencies, which are transmitted into, and propagate through, the longitudinally and angularly defined portions of individual cross-sectional volumetric (three-dimensional) segments, for example, cross-sectional volumetric segments $VS_1$ and $VS_{30}$, of whole roll 10 of paper or of whole pallet 12 of paper, are affected and perturbed by the internal properties and characteristics of, the contents of the volumetric segment portions of the cross-sectional volumetric segments, and therefore, the parameters (amplitude, phase) of the propagating microwaves are a function of the internal properties and characteristics of, the contents of the volumetric segment portions of cross-sectional volumetric segments of whole roll 10 of paper or of whole pallet 12 of paper.

The parameters (amplitude, phase) of both the transmitted microwaves and the received microwaves are used for calculating the microwave differential parameters of amplitude attenuation and phase shift, which in turn, are used for calculating and determining values, relationships, two-dimensional graphs and maps, and, three-dimensional volumetric graphs and maps, of the internal properties and characteristics, such as moisture content, density, material uniformity, and, defects and types thereof, and variabilities thereof, of at least part of whole roll 10 of paper or of whole pallet 12 of paper.

'Test' values of the microwave differential parameters, amplitude attenuation and phase shift, are calculated by analyzing the transmitted and received microwaves. This data is compared to 'calibration' values of corresponding microwave differential parameters obtained from a similarly analyzed reference roll or pallet of paper having known internal properties and characteristics. The sets of test and calibration microwave differential parameter data, along with sophisticated software based automatic pattern recognition (APR) and classification data analysis techniques, are used for generating meaningful data and information, in particular, values, relationships, two-dimensional graphs and maps, and, three-dimensional volumetric graphs and maps, of the internal properties and characteristics, such as moisture content, density, material uniformity, and, defects and types thereof, and variabilities thereof, of at least part of whole roll 10 of paper or of whole pallet 12 of paper.

Figure 5A:
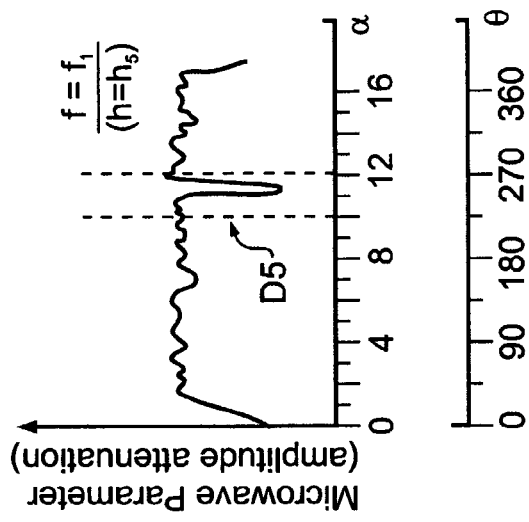
FIGS. 5a and 5b are schematic diagrams illustrating exemplary graphical plots of microwave amplitude attenuation (as an exemplary calculated microwave differential parameter), as a function of multiples of an exemplary constant angular step size α (22.5°, corresponding to sixteen (16) equally sized angular steps of rotation (θ position)) circumscribing around a same cross-sectional volumetric segment $VS_i$, at the first (1-st) and thirtieth (30-th) longitudinal (h-axis) positions, $h_1$ (FIG. 5a) and $h_5$ (FIG. 5b), respectively, of whole roll 10 of paper or whole pallet 12 of paper, obtained by using a constant transmitted microwave frequency, $f=f_1$, in accordance with the present invention.
Figure 5B:
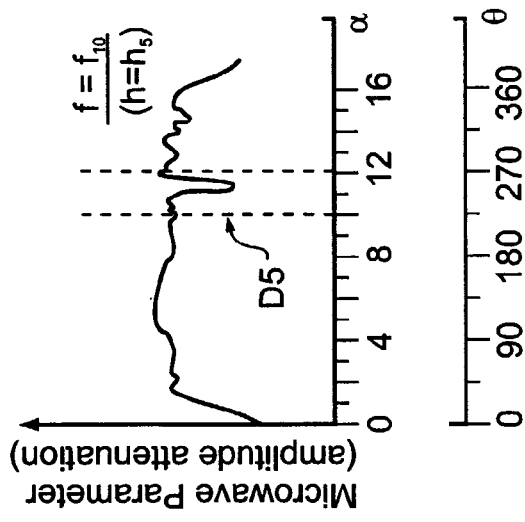

FIGS. 5a and 5b are schematic diagrams illustrating exemplary graphical plots of microwave amplitude attenuation (as an exemplary calculated microwave differential parameter), as a function of multiples of an exemplary constant angular step size $\alpha$ (22.5°, corresponding to sixteen (16) equally sized angular steps of rotation ($\theta$ position)) circumscribing around a same cross-sectional volumetric segment $VS_i$, at the first (1-st) and thirtieth (30-th) longitudinal (h-axis) positions, $h_1$ (FIG. 5a) and $h_5$ (FIG. 5b), respectively, of whole roll 10 of paper or whole pallet 12 of paper, obtained by using a constant transmitted microwave frequency, $f=f_1$.

Figure 5C:
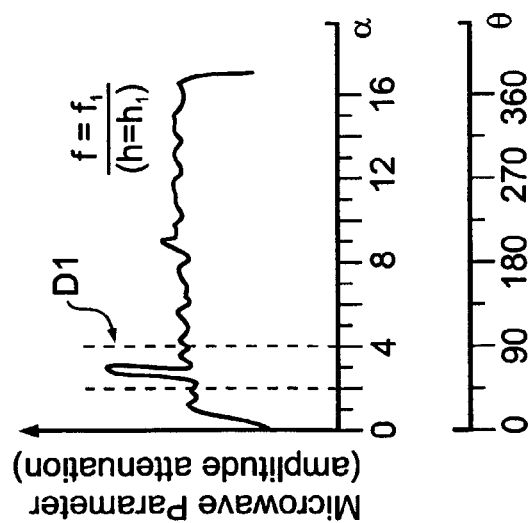
FIGS. 5c and 5d are schematic diagrams illustrating exemplary graphical plots of microwave amplitude attenuation (as an exemplary calculated microwave differential parameter), as a function of multiples of an exemplary constant angular step size α (22.5°, corresponding to sixteen (16) equally sized angular steps of rotation (θ position)) circumscribing around a same cross-sectional volumetric segment $VS_i$, at the first (1-st) and thirtieth (30-th) longitudinal (h-axis) positions, $h_1$ (FIG. 5a) and $h_5$ (FIG. 5b), respectively, of whole roll 10 of paper or whole pallet 12 of paper, obtained by using a constant transmitted microwave frequency, $f=f_{10}$, in accordance with the present invention.
Figure 5D:
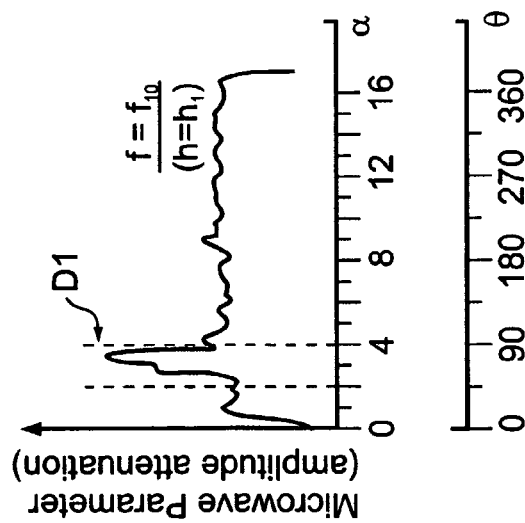

FIGS. 5c and 5d are schematic diagrams illustrating exemplary graphical plots of microwave amplitude attenuation (as an exemplary calculated microwave differential parameter), as a function of multiples of an exemplary constant angular step size $\alpha$ (22.5°, corresponding to sixteen (16) equally sized angular steps of rotation ($\theta$ position)) circumscribing around a same cross-sectional volumetric segment $VS_i$, at the first (1-st) and thirtieth (30-th) longitudinal (h-axis) positions, $h_1$ (FIG. 5a) and $h_5$ (FIG. 5b), respectively, of whole roll 10 of paper or whole pallet 12 of paper, obtained by using another constant transmitted microwave frequency, $f=f_{10}$.

Referring again to FIGS. 1 and 2, each of FIGS. 5a and 5c shows the relatively high increase in microwave attenuation cased by the presence of at least part of anomalous or deviant region D1, whose central, or center-of-gravity, position is associated with central, or center-of-gravity, coordinates ($r_1$, $\theta_1$, and $h_1$), in cross-sectional volumetric segment $VS_1$ of whole roll 10 of paper or whole pallet 12 of paper.

Additionally, each of FIGS. 5b and 5d shows the relatively high decrease in microwave attenuation cased by the presence of at least part of anomalous or deviant region D5, whose central, or center-of-gravity, position is associated with central, or center-of-gravity, coordinates ($r_5$, $\theta_5$, and $h_5$), in cross-sectional volumetric segment $VS_{30}$ of whole roll 10 of paper or whole pallet 12 of paper.

The results shown in FIGS. 5a through 5d indicate that anomalous or deviant regions D1 and D5 may have arisen as a result of the presence of non-uniformities or/and defects in the bulk wood pulp or/and wood chips used as raw materials for manufacturing whole roll 10 of paper or of whole pallet 12 of paper in the paper mill, or/and may have arisen as a result of some anomaly or defect, for example, excess air or/and a foreign object, introduced during the manufacturing process.

The method of the present invention enables, and further includes, three-dimensional volumetric mapping of internal properties and characteristics, such as moisture content, density, material uniformity, and, defects and types thereof, and variabilities thereof, of at least part of a whole roll or pallet of paper.

Implementation of this aspect of the present invention leads to generating a three-dimensional volumetric map of internal properties and characteristics, such as moisture content, density, material uniformity, and, defects and types thereof, and variabilities thereof, of at least part of whole roll 10 of paper or of whole pallet 12 of paper.

Figure 6:
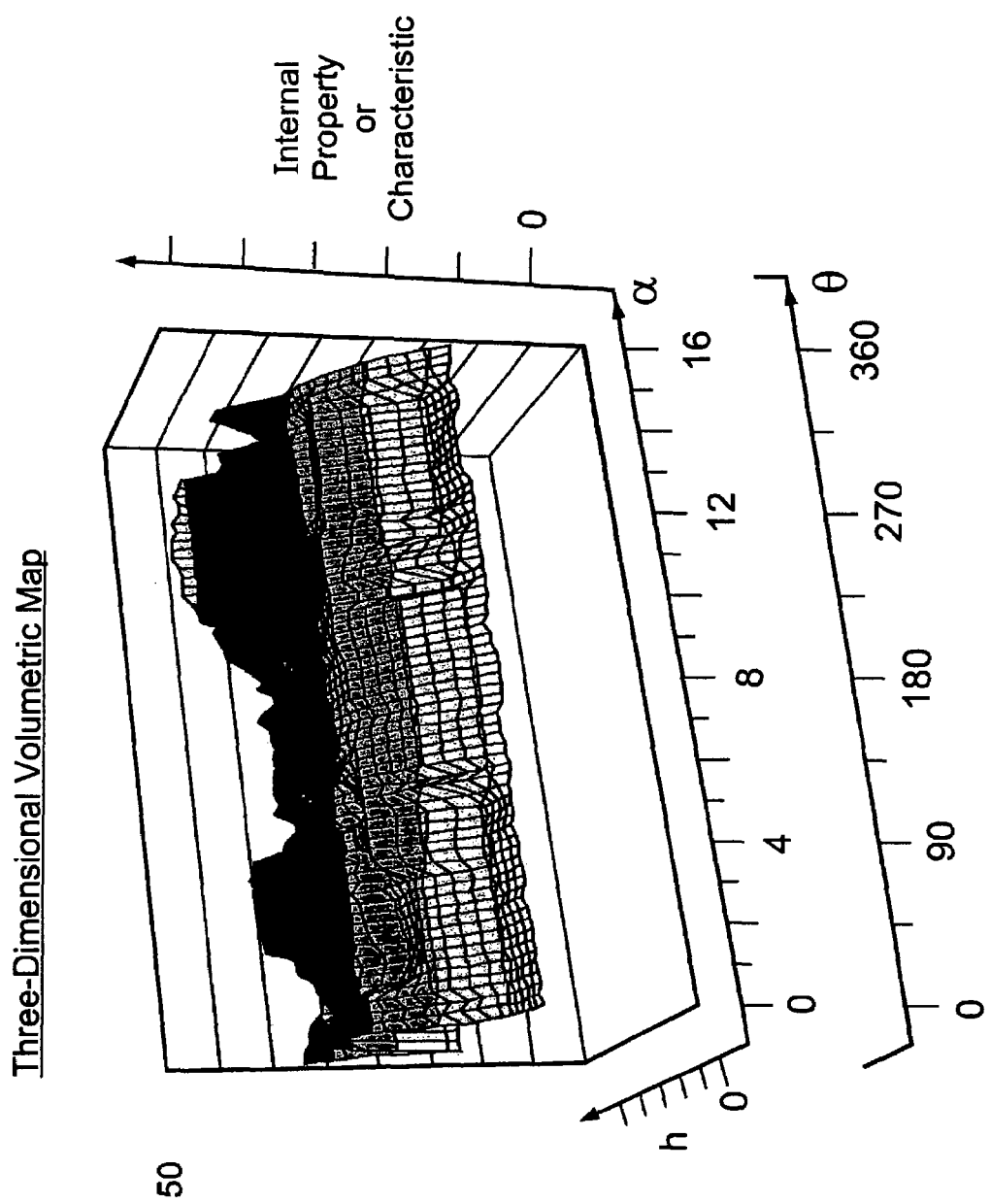
FIG. 6 is a schematic diagram illustrating an exemplary three-dimensional volumetric graphical (contour) plot or map of an exemplary internal property or characteristic, such as moisture content, density, or material uniformity, as a function of multiples of an exemplary constant angular step size α (22.5°, corresponding to sixteen (16) equally sized angular steps of rotation (θ position)) circumscribing around a same cross-sectional volumetric segment $VS_i$, and as a function of longitudinal (h-axis) positions extending along the longitudinal axis (L or L'), of at least part of whole roll 10 of paper or of whole pallet 12 of paper, in accordance with the present invention.

For example, FIG. 6 is a schematic diagram illustrating an exemplary three-dimensional volumetric graphical (contour) plot or map 50 of an exemplary internal property or characteristic, such as moisture content, density, or material uniformity, as a function of multiples of an exemplary constant angular step size $\alpha$ (22.5°, corresponding to sixteen (16) equally sized angular steps of rotation ($\theta$ position)) circumscribing around a same cross-sectional volumetric segment $VS_i$, and as a function of longitudinal (h-axis) positions extending along the longitudinal axis (L or L'), of at least part of whole roll 10 of paper or of whole pallet 12 of paper.

The above illustratively described generated data and information characterizing whole roll 10 of paper or of whole pallet 12 of paper are directly applicable for optimally designing, performing, validating, analyzing, monitoring, QC/QA testing, controlling, and troubleshooting, of an overall commercial paper or paper product manufacturing process, in a 'smart' (accurate, precise, and cost effective) manner. Data and information obtained from the quality control and quality assurance procedures would then be used for controlling or/and adjusting the internal properties and characteristics of whole roll 10 of paper or whole pallet 12 of paper, such as by employing process control and process feedback procedures, prior to whole roll 10 of paper or whole pallet 12 of paper being sent to, or used in, the next manufacturing process or storage, in order to assure proper characteristics and performance of finished paper or finished paper products manufactured from whole roll 10 of paper or whole pallet 12 of paper.

Based upon the above indicated aspects of novelty and inventiveness, and, beneficial and advantageous aspects, characteristics, or features, the present invention successfully overcomes limitations, and widens the scope, of presently known methods of measuring and analyzing internal properties and characteristics, such as moisture content, density, material uniformity, and, defects and types thereof, and variabilities thereof, of commercial sized whole rolls or pallets of paper.

It is appreciated that certain aspects and characteristics of the invention, which are, for clarity, described in the context of separate embodiments, may also be provided in combination in a single embodiment. Conversely, various aspects and characteristics of the invention, which are, for brevity, described in the context of a single embodiment, may also be provided separately or in any suitable sub-combination.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

While the invention has been described in conjunction with specific embodiments and examples thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method of bi-directional (longitudinal and angular) three-dimensional microwave scanning of a whole roll or pallet of paper, comprising the steps of:
   (a) transmitting microwaves into a portion of a cross-sectional volumetric segment of the whole roll or pallet of paper, wherein said cross-sectional volumetric segment lies in a plane perpendicular to, and is centered around a longitudinal position located along, longitudinal axis of the roll or pallet of paper, such that said transmitted microwaves propagate within and through said portion, for forming transmitted microwaves associated with said portion of said volumetric segment;
   (b) receiving at least a portion of said propagating microwaves exiting opposite side of said volumetric segment, for forming received microwaves associated with said portion of said volumetric segment;
   (c) repeating steps (a) and (b), at end of each of a plurality of angular step sizes circumscribing around said volumetric segment, for forming a plurality of paired transmitted and received microwaves associated with a respective plurality of new portions of said volumetric segment, such that said portion and said new portions of said volumetric segment are each associated with a different angular position circumscribing around same said volumetric segment; and
   (d) repeating steps (a) through (c), for a plurality of longitudinal step sizes longitudinally extending along said longitudinal axis of the roll or pallet of paper, wherein each said step size is associated with a respective new cross-sectional volumetric segment lying in a plane perpendicular to, and centered around a new longitudinal position located along, said longitudinal axis of the roll or pallet of paper, for forming a new plurality of said paired transmitted and received microwaves associated with said different angular positions circumscribing around each same said new volumetric segment, for each of a plurality of said new volumetric segments, thereby completing a three-dimensional microwave scan of at least a part of the whole roll or pallet of paper.

2. The method of claim 1, wherein said microwaves have a frequency in a range of between about 1 GHz and about 30 GHz.

3. The method of claim 1, wherein for the whole roll or pallet of paper whose total diameter or total width, through which said transmitted microwaves propagate and exit, is on order of about 1 meter (100 centimeters), said microwaves have a frequency in a range of between about 1 GHz and about 5 GHz.

4. The method of claim 1, wherein for the whole roll or pallet of paper whose total diameter or total width, through which said transmitted microwaves propagate and exit, is on order of about 0.1 meter (10 centimeters), said microwaves have a frequency in a range of between about 10 GHz and about 30 GHz.

5. The method of claim 1, wherein step (c), there is using a constant or variable number of angular steps, at a constant or variable said angular step size, circumscribing around said volumetric segment.

6. The method of claim 1, wherein step (d), there is using a constant or variable said longitudinal step size incrementally extending along said longitudinal axis of the whole roll or pallet of paper.

7. The method of claim 1, wherein said transmitted microwaves propagating within and through a said portion of a said volumetric segment are of a constant amplitude, with a constant frequency.

8. The method of claim 1, wherein said transmitted microwaves propagating within and through a said portion of a said volumetric segment are of a constant amplitude, with a variable frequency.

9. The method of claim 1, wherein said transmitted microwaves propagating within and through a said portion of a said volumetric segment are of a variable amplitude, with a variable frequency.

10. The method of claim 1, wherein said transmitted microwaves propagating within and through a said portion of a said volumetric segment are varied according to a frequency hopping type of variable microwave frequency.

11. The method of claim 1, wherein parameters (amplitude, phase) of said transmitted microwaves and said received microwaves are used for calculating microwave differential parameters of amplitude attenuation and phase shift.

12. The method of claim 11, wherein said amplitude attenuation and said phase shift are used for calculating and determining values of internal properties and characteristics of said at least part of the whole roll or pallet of paper.

13. The method of claim 12, wherein said internal properties and characteristics are selected from the group consisting of moisture content, density, material uniformity, and, defects and types thereof, and variabilities thereof, of said at least part of the whole roll or pallet of paper.

14. The method of claim 11, wherein said amplitude attenuation and said phase shift are used for calculating and determining two-dimensional graphs and maps, and, three-dimensional volumetric graphs and maps, of internal properties and characteristics of said at least part of the whole roll or pallet of paper.

15. The method of claim 14, wherein said internal properties and characteristics are selected from the group consisting of moisture content, density, material uniformity, and, defects and types thereof, and variabilities thereof, of said at least part of the whole roll or pallet of paper.

16. A method of three-dimensional volumetric mapping of internal properties and characteristics of a whole roll or pallet of paper, comprising the steps of:
   (a) transmitting microwaves into a portion of a cross-sectional volumetric segment of the whole roll or pallet of paper, wherein said cross-sectional volumetric segment lies in a plane perpendicular to, and is centered around a longitudinal position located along, longitudinal axis of the roll or pallet of paper, such that said transmitted microwaves propagate within and through said portion, for forming transmitted microwaves associated with said portion of said volumetric segment;

(b) receiving at least a portion of said propagating microwaves exiting opposite side of said volumetric segment, for forming received microwaves associated with said portion of said volumetric segment;

(c) repeating steps (a) and (b), at end of each of a plurality of angular step sizes circumscribing around said volumetric segment, for forming a plurality of paired transmitted and received microwaves associated with a respective plurality of new portions of said volumetric segment, such that said portion and said new portions of said volumetric segment are each associated with a different angular position circumscribing around same said volumetric segment;

(d) repeating steps (a) through (c), for a plurality of longitudinal step sizes longitudinally extending along said longitudinal axis of the roll or pallet of paper, wherein each said step size is associated with a respective new cross-sectional volumetric segment lying in a plane perpendicular to, and centered around a new longitudinal position located along, said longitudinal axis of the roll or pallet of paper, for forming a new plurality of said paired transmitted and received microwaves associated with said different angular positions circumscribing around each same said new volumetric segment, for each of a plurality of said new volumetric segments, thereby completing a three-dimensional microwave scan of at least a part of the whole roll or pallet of paper; and (e) using a set of said pluralities of said paired transmitted and received microwaves associated with said different angular positions circumscribing around each of said volumetric segments of the roll or pallet of paper for the three-dimensional volumetric mapping of the internal properties and characteristics of said at least part of the whole roll or pallet of paper.

17. The method of claim 16, wherein said microwaves have a frequency in a range of between about 1 GHz and about 30 GHz.

18. The method of claim 16, wherein for the whole roll or pallet of paper whose total diameter or total width, through which said transmitted microwaves propagate and exit, is on order of about 1 meter (100 centimeters), said microwaves have a frequency in a range of between about 1 GHz and about 5 GHz.

19. The method of claim 16, wherein for the whole roll or pallet of paper whose total diameter or total width, through which said transmitted microwaves propagate and exit, is on order of about 0.1 meter (10 centimeters), said microwaves have a frequency in a range of between about 10 GHz and about 30 GHz.

20. The method of claim 16, wherein step (c), there is using a constant or variable number of angular steps, at a constant or variable said angular step size, circumscribing around said volumetric segment.

21. The method of claim 16, wherein step (d), there is using a constant or variable said longitudinal step size incrementally extending along said longitudinal axis of the whole roll or pallet of paper.

22. The method of claim 16, wherein said transmitted microwaves propagating within and through a said portion of a said volumetric segment are of a constant amplitude, with a constant frequency.

23. The method of claim 16, wherein said transmitted microwaves propagating within and through a said portion of a said volumetric segment are of a constant amplitude, with a variable frequency.

24. The method of claim 16, wherein said transmitted microwaves propagating within and through a said portion of a said volumetric segment are of a variable amplitude, with a variable frequency.

25. The method of claim 16, wherein said transmitted microwaves propagating within and through a said portion of a said volumetric segment are varied according to a frequency hopping type of variable microwave frequency.

26. The method of claim 16, wherein parameters (amplitude, phase) of said transmitted microwaves and said received microwaves are used for calculating microwave differential parameters of amplitude attenuation and phase shift.

27. The method of claim 26, wherein said amplitude attenuation and said phase shift are used for calculating and determining values of the internal properties and characteristics of said at least part of the whole roll or pallet of paper.

28. The method of claim 16, wherein step (e) the internal properties and characteristics of said at least part of the whole roll or pallet of paper are selected from the group consisting of moisture content, density, material uniformity, and, defects and types thereof, and variabilities thereof.

* * * * *